(12) United States Patent
Scheib et al.

(10) Patent No.: US 10,499,912 B2
(45) Date of Patent: Dec. 10, 2019

(54) APPARATUS FOR HYDRAULIC ASSISTED FRACTURE OF LIVER PARENCHYMA

(71) Applicant: Ethicon Endo-Surgery, LLC, Guaynabo, PR (US)

(72) Inventors: Charles J. Scheib, Loveland, OH (US); Mark S. Zeiner, Mason, OH (US); Michael J. Vendely, Lebanon, OH (US)

(73) Assignee: Ethicon LLC, Guaynabo, PR (US)

( * ) Notice: Subject to any disclaimer, the term of this patent is extended or adjusted under 35 U.S.C. 154(b) by 416 days.

(21) Appl. No.: 15/208,863

(22) Filed: Jul. 13, 2016

(65) Prior Publication Data

US 2018/0014826 A1 Jan. 18, 2018

(51) Int. Cl.
*A61B 17/068* (2006.01)
*A61B 17/00* (2006.01)
(Continued)

(52) U.S. Cl.
CPC .... *A61B 17/0686* (2013.01); *A61B 17/00234* (2013.01); *A61B 17/07207* (2013.01); *A61B 17/295* (2013.01); *A61B 2017/00353* (2013.01); *A61B 2017/00424* (2013.01); *A61B 2017/00539* (2013.01); *A61B 2017/00544* (2013.01); *A61B 2017/00557* (2013.01);
(Continued)

(58) Field of Classification Search
CPC .......... A61B 17/00234; A61B 17/0686; A61B 2017/320048; A61B 2017/00557; A61B 2017/00539; A61B 2017/00353
USPC .......................................... 227/175.1–182.1
See application file for complete search history.

(56) References Cited

U.S. PATENT DOCUMENTS

| 4,805,823 A | 2/1989 | Rothfuss |
| 5,018,657 A * | 5/1991 | Pedlick ............... A61B 17/072 |
| | | 227/130 |

(Continued)

FOREIGN PATENT DOCUMENTS

| EP | 1 785 098 A2 | 5/2007 |
| EP | 1 997 439 A2 | 12/2008 |

(Continued)

OTHER PUBLICATIONS

U.S. Appl. No. 14/810,786, filed Jul. 29, 2015.

(Continued)

*Primary Examiner* — Robert F Long
*Assistant Examiner* — Xavier A Madison
(74) *Attorney, Agent, or Firm* — Frost Brown Todd LLC

(57) ABSTRACT

A surgical instrument and method of operating on a tissue includes a shaft assembly and an end effector. The end effector extends in a longitudinal direction from the shaft assembly and has a first jaw, a second jaw, and a deformable hydraulic member. The second jaw is movably mounted relative to the first jaw and is configured to transition between an open configuration and a closed configuration. The first and second jaws are thus configured to have the tissue positioned therebetween in the closed configuration. The deformable hydraulic is configured to contain a fluid. With the fluid contained in the deformable hydraulic member, the deformable hydraulic member is configured to sever the tissue positioned between the first and second jaws in the closed configuration.

20 Claims, 21 Drawing Sheets

(51) Int. Cl.
*A61B 17/072* (2006.01)
*A61B 17/295* (2006.01)
*A61B 17/32* (2006.01)

(52) U.S. Cl.
CPC .............. *A61B 2017/07214* (2013.01); *A61B 2017/07221* (2013.01); *A61B 2017/07271* (2013.01); *A61B 2017/07285* (2013.01); *A61B 2017/320048* (2013.01)

(56) References Cited

U.S. PATENT DOCUMENTS

| | | | |
|---|---|---|---|
| 5,415,334 A | 5/1995 | Williamson et al. | |
| 5,465,895 A | 11/1995 | Knodel et al. | |
| 5,597,107 A | 1/1997 | Knodel et al. | |
| 5,632,432 A | 5/1997 | Schulze et al. | |
| 5,673,840 A | 10/1997 | Schulze et al. | |
| 5,704,534 A | 1/1998 | Huitema et al. | |
| 5,792,135 A | 8/1998 | Madhani et al. | |
| 5,814,055 A | 9/1998 | Knodel et al. | |
| 5,817,084 A | 10/1998 | Jensen | |
| 5,878,193 A | 3/1999 | Wang et al. | |
| 6,231,565 B1 | 5/2001 | Tovey et al. | |
| 6,364,888 B1 | 4/2002 | Niemeyer et al. | |
| 6,783,524 B2 | 8/2004 | Anderson et al. | |
| 6,978,921 B2 | 12/2005 | Shelton et al. | |
| 7,000,818 B2 | 2/2006 | Shelton et al. | |
| 7,143,923 B2 | 12/2006 | Shelton et al. | |
| 7,303,108 B2 | 12/2007 | Shelton | |
| 7,367,485 B2 | 5/2008 | Shelton et al. | |
| 7,380,695 B2 | 6/2008 | Doll et al. | |
| 7,380,696 B2 | 6/2008 | Shelton et al. | |
| 7,404,508 B2 | 7/2008 | Smith et al. | |
| 7,434,715 B2 | 10/2008 | Shelton et al. | |
| 7,524,320 B2 | 4/2009 | Tierney et al. | |
| 7,691,098 B2 | 4/2010 | Wallace et al. | |
| 7,721,930 B2 | 5/2010 | McKenna et al. | |
| 7,806,891 B2 | 10/2010 | Nowlin et al. | |
| 8,210,411 B2 | 7/2012 | Yates et al. | |
| 8,408,439 B2 | 4/2013 | Huang et al. | |
| 8,453,914 B2 | 6/2013 | Laurent et al. | |
| 8,479,969 B2 | 7/2013 | Shelton | |
| 8,573,461 B2 | 11/2013 | Shelton et al. | |
| 8,573,465 B2 | 11/2013 | Shelton | |
| 8,602,288 B2 | 12/2013 | Shelton et al. | |
| 8,616,431 B2 | 12/2013 | Timm | |
| 8,783,541 B2 | 7/2014 | Shelton et al. | |
| 8,800,838 B2 | 8/2014 | Shelton | |
| 8,820,605 B2 | 9/2014 | Shelton | |
| 8,844,789 B2 | 9/2014 | Shelton et al. | |
| 9,186,142 B2 | 11/2015 | Fanelli et al. | |
| 9,301,759 B2 | 4/2016 | Spivey et al. | |
| 2003/0111507 A1 | 6/2003 | Nunez | |
| 2007/0021761 A1* | 1/2007 | Phillips | A61B 17/122 606/157 |
| 2010/0243706 A1* | 9/2010 | Cohen | A61B 17/07207 227/176.1 |
| 2014/0239036 A1 | 8/2014 | Zerkle et al. | |
| 2014/0239037 A1 | 8/2014 | Boudreaux et al. | |
| 2014/0239038 A1 | 8/2014 | Leimbach et al. | |
| 2014/0239040 A1 | 8/2014 | Fanelli et al. | |
| 2014/0239041 A1 | 8/2014 | Zerkle et al. | |
| 2014/0239042 A1 | 8/2014 | Simms et al. | |
| 2014/0239043 A1 | 8/2014 | Simms et al. | |
| 2014/0239044 A1 | 8/2014 | Hoffman | |
| 2015/0272575 A1 | 10/2015 | Leimbach et al. | |
| 2015/0374360 A1 | 12/2015 | Scheib et al. | |
| 2015/0374373 A1 | 12/2015 | Rector et al. | |

FOREIGN PATENT DOCUMENTS

| | | |
|---|---|---|
| EP | 2 674 111 A2 | 12/2013 |
| ID | 10 2007 059064 A1 | 6/2009 |
| WO | WO 02/17799 A1 | 3/2002 |

OTHER PUBLICATIONS

U.S. Appl. No. 14/884,272, filed Oct. 15, 2015.
European Search Report and Written Opinion dated Sep. 25, 2017 for Application No. EP 17181042.7, 8 pgs.
International Search Report and Written Opinion dated Sep. 25, 2017 for Application No. PCT/US2017/041637, 15 pgs.

\* cited by examiner

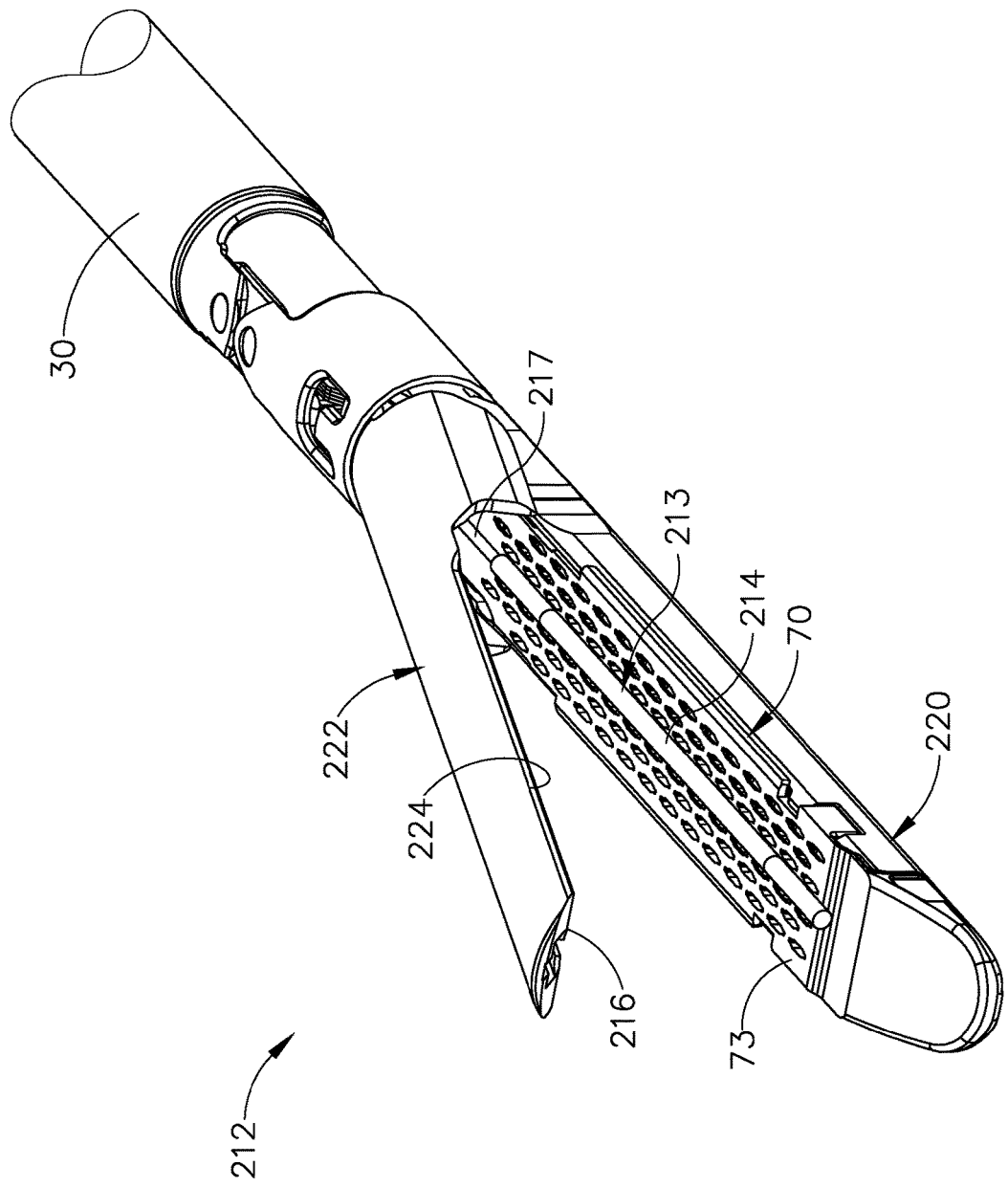

APPARATUS FOR HYDRAULIC ASSISTED FRACTURE OF LIVER PARENCHYMA

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasonic vibration, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. patents is incorporated by reference herein.

While the surgical staplers referred to above are described as being used in endoscopic procedures, it should be understood that such surgical staplers may also be used in open procedures and/or other non-endoscopic procedures. By way of example only, a surgical stapler may be inserted through a thoracotomy, and thereby between a patient's ribs, to reach one or more organs in a thoracic surgical procedure that does not use a trocar as a conduit for the stapler. Such procedures may include the use of the stapler to sever and close a vessel leading to a lung. For instance, the vessels leading to an organ may be severed and closed by a stapler before removal of the organ from the thoracic cavity. Of course, surgical staplers may be used in various other settings and procedures.

Examples of surgical staplers that may be particularly suited or use through a thoracotomy are disclosed in U.S. patent application Ser. No. 14/810,786, entitled "Surgical Staple Cartridge with Compression Feature at Knife Slot," filed Jul. 29, 2015, issued as U.S. Pat. No. 10,314,580 on Jun. 11, 2019; U.S. Patent Pub. No. 2014/0243801, entitled "Surgical Instrument End Effector Articulation Drive with Pinion and Opposing Racks," published Aug. 28, 2014, issued as U.S. Pat. No. 9,186,142 on Nov. 17, 2015; U.S. Patent Pub. No. 2014/0239041, entitled "Lockout Feature for Movable Cutting Member of Surgical Instrument," published Aug. 28, 2014, issued as U.S. Pat. No. 9,717,497 on Aug. 1, 2017; U.S. Patent Pub. No. 2014/0239042, entitled "Integrated Tissue Positioning and Jaw Alignment Features for Surgical Stapler," published Aug. 28, 2014, issued as U.S. Pat. No. 9,517,065 on Dec. 13, 2016; U.S. Patent Pub. No. 2014/0239036, entitled "Jaw Closure Feature for End Effector of Surgical Instrument," published Aug. 28, 2014, issued as U.S. Pat. No. 9,839,421 on Dec. 12, 2017; U.S. Patent Pub. No. 2014/0239040, entitled "Surgical Instrument with Articulation Lock having a Detenting Binary Spring," published Aug. 28, 2014, issued as U.S. Pat. No. 9,867,615 on Jan. 16, 2018; U.S. Patent Pub. No. 2014/0239043, entitled "Distal Tip Features for End Effector of Surgical Instrument," published Aug. 28, 2014, issued as U.S. Pat. No. 9,622,746 on Apr. 18, 2017; U.S. Patent Pub. No. 2014/0239037, entitled "Staple Forming Features for Surgical Stapling Instrument," published Aug. 28, 2014, issued as U.S. Pat. No. 10,092,292 on Oct. 9, 2018; U.S. Patent Pub. No. 2014/0239038, entitled "Surgical Instrument with Multi-Diameter Shaft," published Aug. 28, 2014, issued as U.S. Pat. No. 9,795,379 on Oct. 24, 2017; and U.S. Patent Pub. No. 2014/0239044, entitled "Installation Features for Surgical Instrument End Effector Cartridge," published Aug. 28, 2014, issued as U.S. Pat. No. 9,808,248 on Nov. 7, 2017. The disclosure of each of the above-cited U.S. Patent Applications is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 8 depicts a perspective view of the end effector of FIG. 7, with the end effector in an open configuration;

Figure 1:
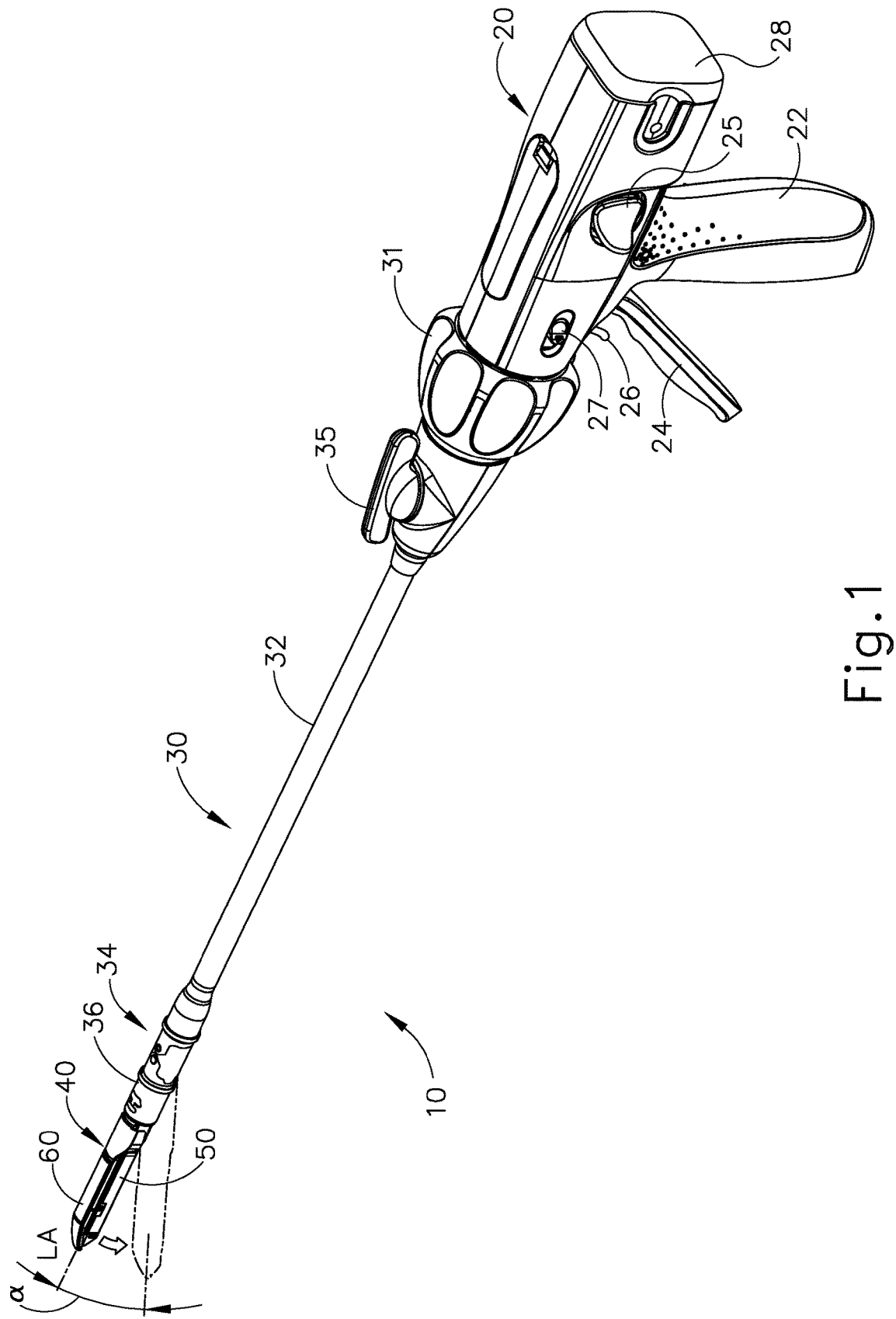
FIG. 1 depicts a perspective view of an exemplary articulating surgical stapling instrument having a first exemplary end effector.

The drawings are not intended to be limiting in any way, and it is contemplated that various embodiments of the invention may be carried out in a variety of other ways, including those not necessarily depicted in the drawings.

The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. EXEMPLARY SURGICAL STAPLER

FIG. 1 depicts an exemplary surgical stapling and severing instrument (10) that includes a handle assembly (20), a shaft assembly (30), and an end effector (40). End effector (40) and the distal portion of shaft assembly (30) are sized for insertion, in a nonarticulated state as depicted in FIG. 1, through a trocar cannula to a surgical site in a patient for performing a surgical procedure. By way of example only, such a trocar may be inserted in a patient's abdomen, between two of the patient's ribs, or elsewhere. In some settings, instrument (10) is used without a trocar. For instance, end effector (40) and the distal portion of shaft assembly (30) may be inserted directly through a thoracotomy or other type of incision. It should be understood that terms such as "proximal" and "distal" are used herein with reference to a clinician gripping handle assembly (20) of instrument (10). Thus, end effector (40) is distal with respect to the more proximal handle assembly (20). It will be further appreciated that for convenience and clarity, spatial terms such as "vertical" and "horizontal" are used herein with respect to the drawings. However, surgical instruments are used in many orientations and positions, and these terms are not intended to be limiting and absolute.

A. Exemplary Handle Assembly and Shaft Assembly

As shown in FIG. 1, handle assembly (20) of the present example comprises pistol grip (22), a closure trigger (24), and a firing trigger (26). Each trigger (24, 26) is selectively pivotable toward and away from pistol grip (22) as will be described in greater detail below. Handle assembly (20) further includes an anvil release button (25), a firing beam reverse switch (27), and a removable battery pack (28). Other suitable configurations for handle assembly (20) will be apparent to those of ordinary skill in the art in view of the teachings herein.

Figure 2:
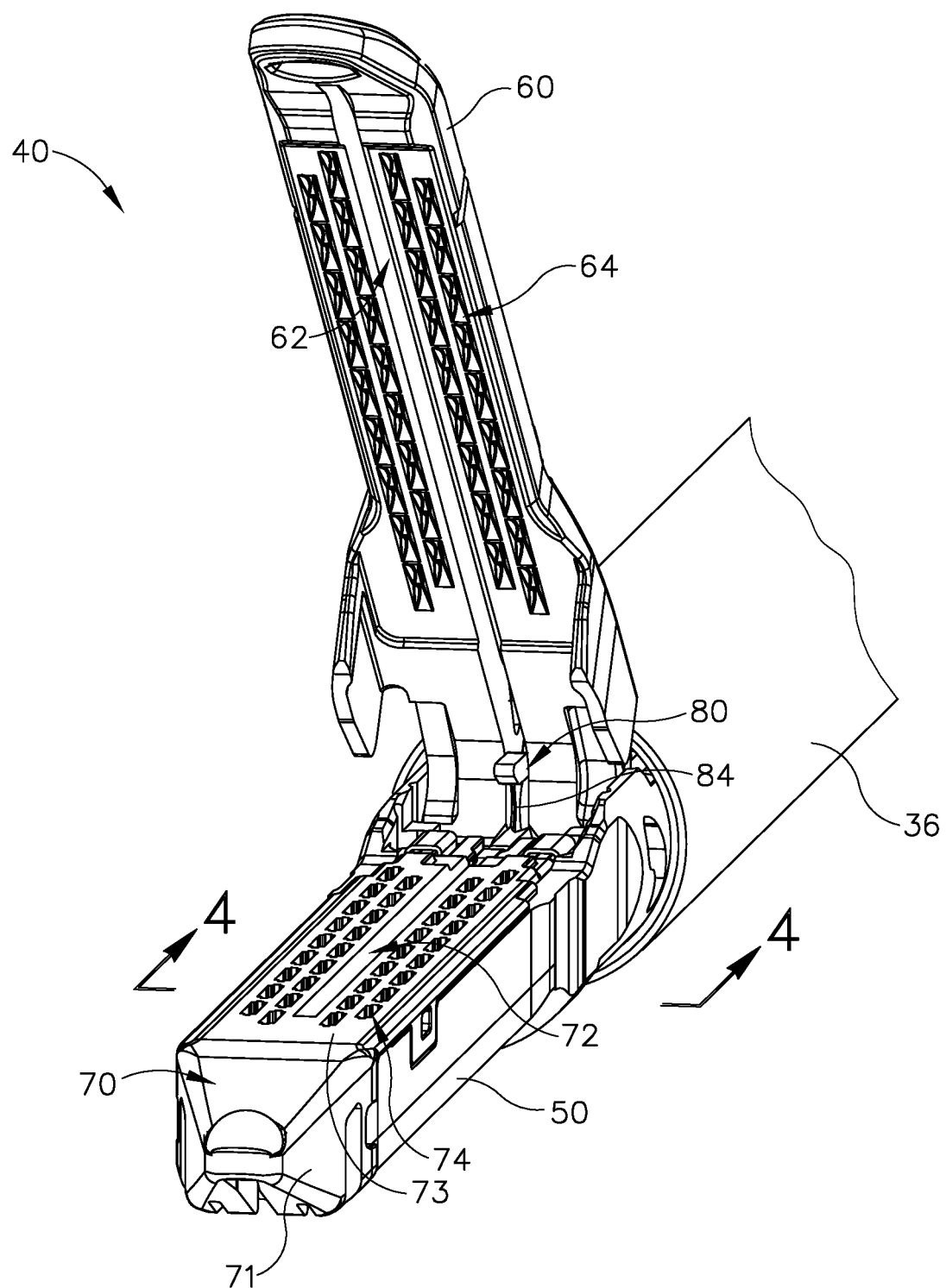
FIG. 2 depicts a perspective view of the end effector of FIG. 1, with the end effector in an open configuration.

As shown in FIGS. 1-2, shaft assembly (30) of the present example comprises an outer closure tube (32), an articulation section (34), and a closure ring (36), which is further coupled with end effector (40). Closure tube (32) extends along the length of shaft assembly (30). Closure ring (36) is positioned distal to articulation section (34). Closure tube (32) and closure ring (36) are configured to translate longitudinally relative to handle assembly (20). Longitudinal translation of closure tube (32) is communicated to closure ring (36) via articulation section (34).

Articulation section (34) is operable to laterally deflect closure ring (36) and end effector (40) laterally away from the longitudinal axis (LA) of shaft assembly (30) at a desired angle (α). In the present example, articulation is controlled through an articulation control knob (35) which is located at the proximal end of shaft assembly (30). Knob (35) is rotatable about an axis that is perpendicular to the longitudinal axis (LA) of shaft assembly (30). Closure ring (36) and end effector (40) pivot about an axis that is perpendicular to the longitudinal axis (LA) of shaft assembly (30) in response to rotation of knob (35). Articulation section (34) is configured to communicate longitudinal translation of closure tube (32) to closure ring (36), regardless of whether articulation section (34) is in a straight configuration or an articulated configuration.

In some versions, articulation section (34) and/or articulation control knob (35) are/is constructed and operable in accordance with at least some of the teachings of U.S. Pub. No. 2014/0243801, entitled "Surgical Instrument End Effector Articulation Drive with Pinion and Opposing Racks," published Aug. 28, 2014, issued as U.S. Pat. No. 9,186,142 on Nov. 17, 2015, the disclosure of which is incorporated by reference herein. Articulation section (34) may also be constructed and operable in accordance with at least some of the teachings of U.S. Pub. No. 2015/0374360, entitled "Articulation Drive Features for Surgical Stapler," published Dec. 31, 2015, issued as U.S. Pat. No. 10,292,701 on May 21, 2019, the disclosure of which is incorporated by reference herein. Other suitable forms that articulation section (34) and articulation knob (35) may take will be apparent to those of ordinary skill in the art in view of the teachings herein.

As shown in FIGS. 1-2, shaft assembly (30) of the present example further includes a rotation knob (31). Rotation knob (31) is operable to rotate the entire shaft assembly (30) and end effector (40) relative to handle assembly (20) about the longitudinal axis (LA) of shaft assembly (30). Of course, shaft assembly (30) may have a variety of other components, features, and operabilities, in addition to or in lieu of any of those noted above. By way of example only, at least part of shaft assembly (30) is constructed in accordance with at least some of the teachings of U.S. Pub. No. 2014/0239038, entitled "Surgical Instrument with Multi-Diameter Shaft," published Aug. 28, 2014, issued as U.S. Pat. No. 9,795,379 on Oct. 24, 2017, the disclosure of which is incorporated by reference herein. Other suitable configurations for shaft assembly (30) will be apparent to those of ordinary skill in the art in view of the teachings herein.

B. Exemplary End Effector

Figure 3:
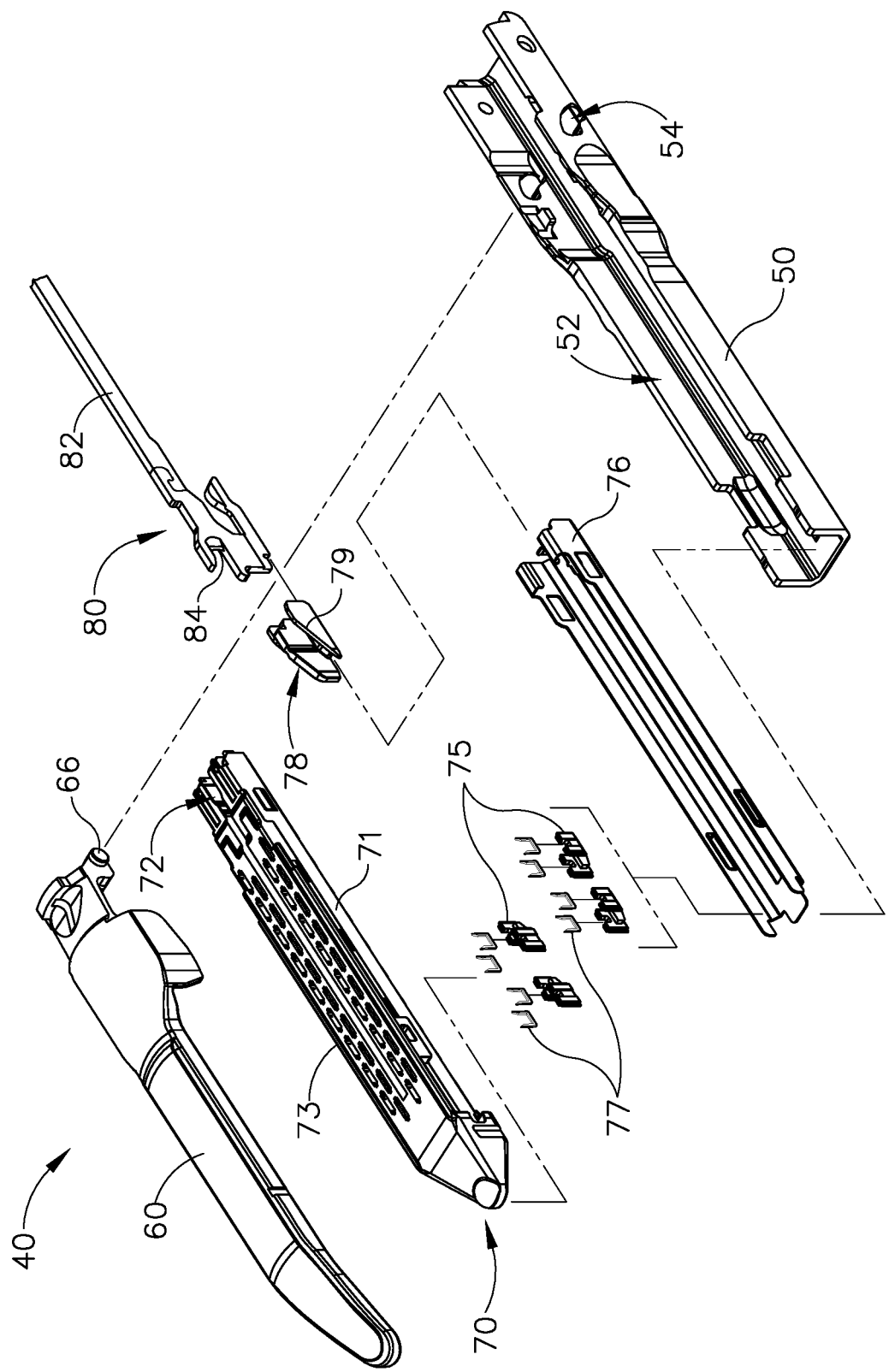
FIG. 3 depicts an exploded perspective view of the end effector of FIG. 2.
Figure 4:
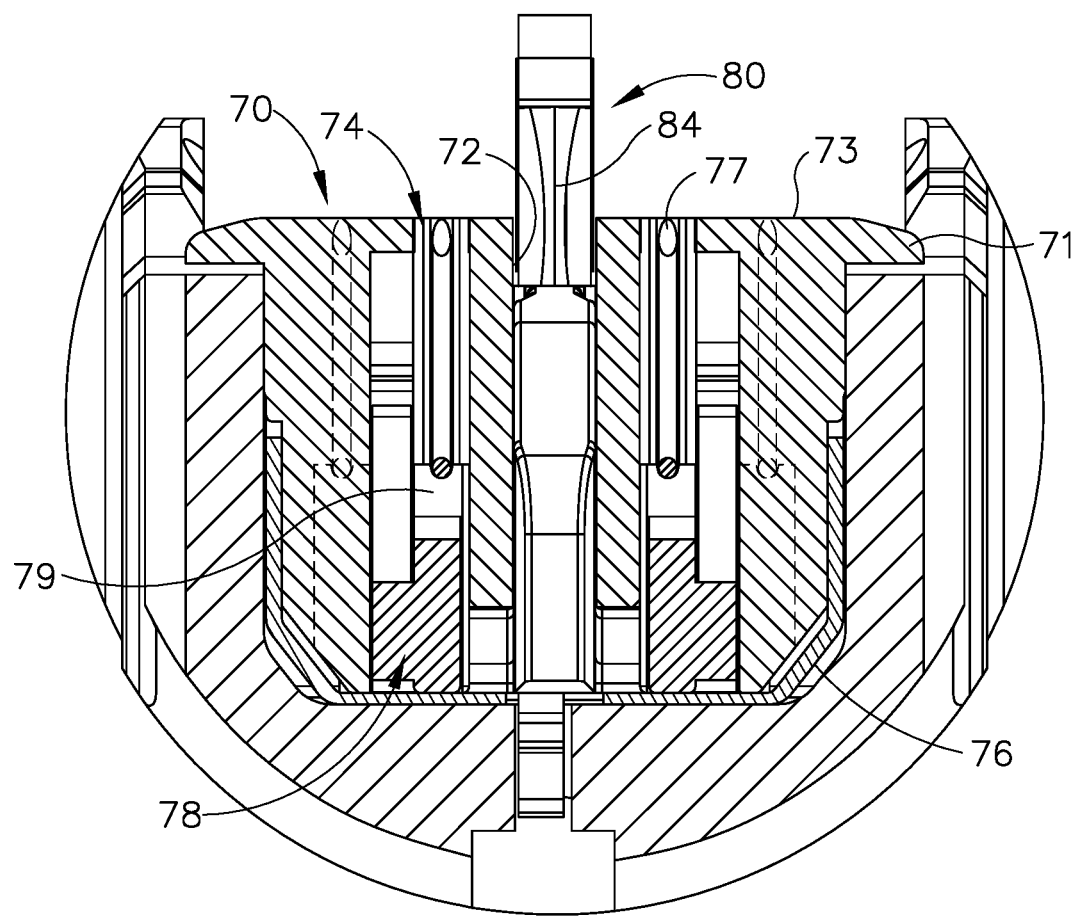
FIG. 4 depicts a cross-sectional end view of the end effector of FIG. 2, taken along line 4-4 of FIG. 2.

As also shown in FIGS. 2-4, end effector (40) of the present example includes a lower jaw (50) and a pivotable anvil (60). Anvil (60) includes a pair of integral, outwardly extending pins (66) that are disposed in corresponding curved slots (54) of lower jaw (50). Anvil (60) is pivotable toward and away from lower jaw (50) between an open position (shown in FIG. 2) and a closed position (shown in FIG. 1). Use of the term "pivotable" (and similar terms with "pivot" as a base) should not be read as necessarily requiring pivotal movement about a fixed axis. For instance, in the present example, anvil (60) pivots about an axis that is defined by pins (66), which slide along curved slots (54) of lower jaw (50) as anvil (60) moves toward lower jaw (50). In such versions, the pivot axis translates along the path defined by slots (54) while anvil (60) simultaneously pivots about that axis. In addition, or in the alternative, the pivot axis may slide along slots (54) first, with anvil (60) then pivoting about the pivot axis after the pivot axis has slid a certain distance along the slots (54). It should be understood that such sliding/translating pivotal movement is encompassed within terms such as "pivot," "pivots," "pivotal," "pivotable," "pivoting," and the like. Of course, some versions may provide pivotal movement of anvil (60) about an axis that remains fixed and does not translate within a slot or channel, etc.

Lower jaw (50) of the present example defines a channel (52) that is configured to receive a staple cartridge (70). Staple cartridge (70) may be inserted into channel (52), end effector (40) may be actuated, and then staple cartridge (70) may be removed and replaced with another staple cartridge (70). Lower jaw (50) thus releasably retains staple cartridge (70) in alignment with anvil (60) for actuation of end effector (40). In some versions, lower jaw (50) is constructed in accordance with at least some of the teachings of U.S. Pub. No. 2014/0239044, entitled "Installation Features for Surgical Instrument End Effector Cartridge," published Aug. 28, 2014, issued as U.S. Pat. No. 9,808,248 on Nov. 7, 2017, the disclosure of which is incorporated by reference herein. Other suitable forms that lower jaw (50) may take will be apparent to those of ordinary skill in the art in view of the teachings herein.

As best seen in FIG. 3, staple cartridge (70) of the present example comprises a cartridge body (71) and a tray (76) secured to the underside of cartridge body (71). The upper side of cartridge body (71) presents a deck (73), against which tissue may be compressed when anvil (60) is in a closed position. Cartridge body (71) further defines a longitudinally extending channel (72) and a plurality of staple pockets (74). A staple (77) is positioned in each staple pocket (74). A staple driver (75) is also positioned in each staple pocket (74), underneath a corresponding staple (77), and above tray (76). As will be described in greater detail below, staple drivers (75) are operable to translate upwardly in staple pockets (74) to thereby drive staples (77) upwardly through staple pockets (74) and into engagement with anvil (60). Staple drivers (75) are driven upwardly by a wedge sled (78), which is captured between cartridge body (71) and tray (76), and which translates longitudinally through cartridge body (71). Wedge sled (78) includes a pair of obliquely angled cam surfaces (79), which are configured to engage staple drivers (75) and thereby drive staple drivers (75) upwardly as wedge sled (78) translates longitudinally through cartridge (70).

By way of example only, staple cartridge (70) may be constructed and operable in accordance with at least some of the teachings of U.S. Pub. No. 2014/0239042, entitled "Integrated Tissue Positioning and Jaw Alignment Features for Surgical Stapler," published Aug. 28, 2014, issued as U.S. Pat. No. 9,517,065 on Dec. 13, 2016, the disclosure of which is incorporated by reference herein; and/or U.S. Pub. No. 2014/0239044, entitled "Installation Features for Surgical Instrument End Effector Cartridge," published Aug. 28, 2014, issued as U.S. Pat. No. 9,808,248 on Nov. 7, 2017, the disclosure of which is incorporated by reference herein. Other suitable forms that staple cartridge (70) may take will be apparent to those of ordinary skill in the art in view of the teachings herein.

Anvil (60) of the present example comprises a longitudinally extending channel (62) and a plurality of staple forming pockets (64). Channel (62) is configured to align with channel (72) of staple cartridge (70) when anvil (60) is in a closed position. Each staple forming pocket (64) is positioned to lie over a corresponding staple pocket (74) of staple cartridge (70) when anvil (60) is in a closed position. Staple forming pockets (64) are configured to deform the legs of staples (77) when staples (77) are driven through tissue and into anvil (60). In particular, staple forming pockets (64) are configured to bend the legs of staples (77) to secure the formed staples (77) in the tissue. By way of example only, anvil (60) may be constructed in accordance with at least some of the teachings of U.S. Pub. No. 2014/0239037, entitled "Staple Forming Features for Surgical Stapling Instrument," published Aug. 28, 2014, issued as U.S. Pat. No. 10,092,292 on Oct. 9, 2018, the disclosure of which is incorporated by reference herein. Other suitable forms that anvil (60) may take will be apparent to those of ordinary skill in the art in view of the teachings herein.

In the present example, knife member (80) is configured to translate through end effector (40). As best seen in FIG. 3, knife member (80) is secured to the distal end of a firing beam (82), which extends through a portion of shaft assembly (30). Knife member (80) is positioned in channels (62, 72) of anvil (60) and staple cartridge (70). Knife member (80) includes a distally presented cutting edge (84) that is configured to sever tissue that is compressed between anvil (60) and deck (73) of staple cartridge (70) as knife member (80) translates distally through end effector (40). Knife member (80) also drives wedge sled (78) distally as knife member (80) translates distally through end effector (40), thereby driving staples (77) through tissue and against anvil (60) into formation.

C. Exemplary Actuation of Anvil

In the present example shown in FIGS. 1-4, anvil (60) is driven toward lower jaw (50) by advancing closure ring (36) distally relative to end effector (40). Closure ring (36) cooperates with anvil (60) through a camming action to drive anvil (60) toward lower jaw (50) in response to distal translation of closure ring (36) relative to end effector (40). Similarly, closure ring (36) may cooperate with anvil (60) to open anvil (60) away from lower jaw (50) in response to proximal translation of closure ring (36) relative to end effector (40). By way of example only, closure ring (36) and anvil (60) may interact in accordance with at least some of the teachings of U.S. Pub. No. 2014/0239036, entitled "Jaw Closure Feature for End Effector of Surgical Instrument," published Aug. 28, 2014, issued as U.S. Pat. No. 9,839,421 on Dec. 12, 2017, the disclosure of which is incorporated by reference herein; and/or in accordance with at least some of the teachings of U.S. Pub. No. 2015/0374373, entitled "Jaw Opening Feature for Surgical Stapler," published Dec. 31, 2015, issued as U.S. Pat. No. 10,335,147 on Jul. 2, 2019, the disclosure of which is incorporated by reference herein. Exemplary features that may be used to provide longitudinal translation of closure ring (36) relative to end effector (40) will be described in greater detail below.

In the present example, closure trigger (24) is pivotable toward pistol grip (22) to drive closure tube (32) and closure ring (36) distally. Various suitable components that may be used to convert pivotal movement of closure trigger (24) toward pistol grip (22) into distal translation of closure tube (32) and closure ring (36) relative to handle assembly (20) will be apparent to those of ordinary skill in the art in view of the teachings herein. When closure trigger (24) reaches a fully pivoted state, such that anvil (60) is in a fully closed position relative to lower jaw (50), locking features in handle assembly (20) lock the position of closure trigger (24) and closure tube (32), thereby locking anvil (60) in a fully closed position relative to lower jaw (50). These locking features are released by actuation of anvil release button (25). Other suitable features that may be used to actuate anvil (60) will be apparent to those of ordinary skill in the art in view of the teachings herein.

D. Exemplary Actuation of Firing Beam

In the present example, instrument (10) includes motorized components that are configured to drive firing beam (82) distally in response to pivoting of firing trigger (26) toward pistol grip (22). In some versions, a motor (not shown) is contained in pistol grip (22) and receives power from battery pack (28). This motor is coupled with a transmission assembly (not shown) that converts rotary motion of a drive shaft of the motor into linear translation of firing beam (82). In some such versions, firing beam (82) may only be advanced distally when anvil (60) is in a fully closed position relative to lower jaw (50). After firing beam (82) is advanced distally to sever tissue and drive staples (77), the drive assembly for firing beam (82) may be automatically reversed to drive firing beam (82) proximally back to the retracted position. Alternatively, the operator may actuate firing beam reverse switch (27), which may reverse the drive assembly for firing beam (82) in order to retract firing beam (82) to a proximal position.

By way of example only, the features that are operable to provide motorized actuation of firing beam (82) may be configured and operable in accordance with at least some of the teachings of U.S. Pat. No. 8,210,411, entitled "Motor-Driven Surgical Instrument," issued Jul. 3, 2012, the disclosure of which is incorporated by reference herein; and/or U.S. Pub. No. 2015/0272575, entitled "Surgical Instrument Comprising a Sensor System," published Oct. 1, 2015, issued as U.S. Pat. No. 9,913,642 on Mar. 13, 2018, the disclosure of which is incorporated by reference herein. Other suitable components, features, and configurations that may be used to provide motorization of firing beam (82) will be apparent to those of ordinary skill in the art in view of the teachings herein. It should also be understood that some other versions may provide manual driving of firing beam (82), such that a motor may be omitted. By way of example only, firing beam (82) may be manually actuated in accordance with at least some of the teachings of any other reference cited herein.

It should also be understood that any other components or features of instrument (10) may be configured and operable in accordance with any of the various references cited herein. Additional exemplary modifications that may be provided for instrument (10) will be described in greater detail below. Various suitable ways in which the below teachings may be incorporated into instrument (10) will be apparent to those of ordinary skill in the art. Similarly, various suitable ways in which the below teachings may be combined with various teachings of the references cited herein will be apparent to those of ordinary skill in the art. It should also be understood that the below teachings are not limited to instrument (10) or devices taught in the references cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. EXEMPLARY SURGICAL STAPLER WITH A CRUSH SURFACE

While the above-described surgical instrument (10) provides one example of an end effector (40) that may be used to staple and sever tissue within a patient, it will be appreciated that the human body includes a wide variety of tissues located in distinct, sometimes difficult to access regions throughout the patient. For example, a liver includes parenchymal tissue including vessels or ducts passing throughout. In settings where the liver includes a tumor, it may be desirable to resect the portion of the liver containing the tumor. The resection may be anatomic (e.g., resection of the right or left side of the liver, inclusive of the lobes on that side) or non-anatomic (e.g., resection of just a single lobe or wedge of liver tissue). This resection process may entail at least three kinds of steps—a first step to dissect the tissue (e.g., liver parenchyma) around the vessels or ducts, to thereby isolate or reveal the vessels or ducts; a second step to ligate those vessels or ducts; and a third step to sever the ligated vessels or ducts.

One method of liver resection includes the well-known Kelly clamp method, where a Kelly style clamp is used to compress the parenchymal liver tissue and thereby dissect the parenchymal tissue through a crushing action. However, treatments may require many instruments to accommodate such a wide variety of tissues and vessels or ducts within the human body, thereby adding to the time and complexity associated with assessing the state of the tissue, selecting and/or changing instruments, and performing the resection. It may therefore be desirable to provide a variation of surgical instrument (10) with an end effector (112) having a pair of crush surfaces (114, 116) that are configured to sever tissue by crushing the tissue; while also providing an adjacent staple cartridge (118) to selectively ligate one or more vessels or ducts passing through the tissue. Thereby, a single surgical instrument will allow the operator to more quickly assess the tissue and proceed with further tissue dissection and/or ligation of vessels and ducts.

The variation of surgical instrument (10) is described below in the context of dissecting liver tissue (e.g., liver parenchyma) with crush surfaces (114, 116) and using staples to ligate associated vessels or ducts (e.g., portal vein, hepatic vein branches, hepatic artery branches, extrahepatic vessels, etc.). In some instances, (e.g., in the case of hepatic vein branches and hepatic artery branches, etc.), the vessel or duct that is sealed by the staples is exposed when the operator crushes the liver tissue with surfaces (114, 116). In some other instances (e.g., in the case of the portal vein and extrahepatic vessels, etc.), the vessel or duct that is sealed by the staples is separate from the liver tissue that the operator has crushed with surfaces (114, 116). While the following description of end effector (112) and method of treatment is provided in the context of liver resection, it will be appreciated that end effector (112) may be alternatively configured to treat any tissue in the human body with similar features. It should also be understood that that the features discussed below may be readily incorporated into surgical instrument (10) discussed above. To this end, like numbers indicate like features described above in greater detail.

A. Exemplary End Effector and Crush Surface

Figure 5:
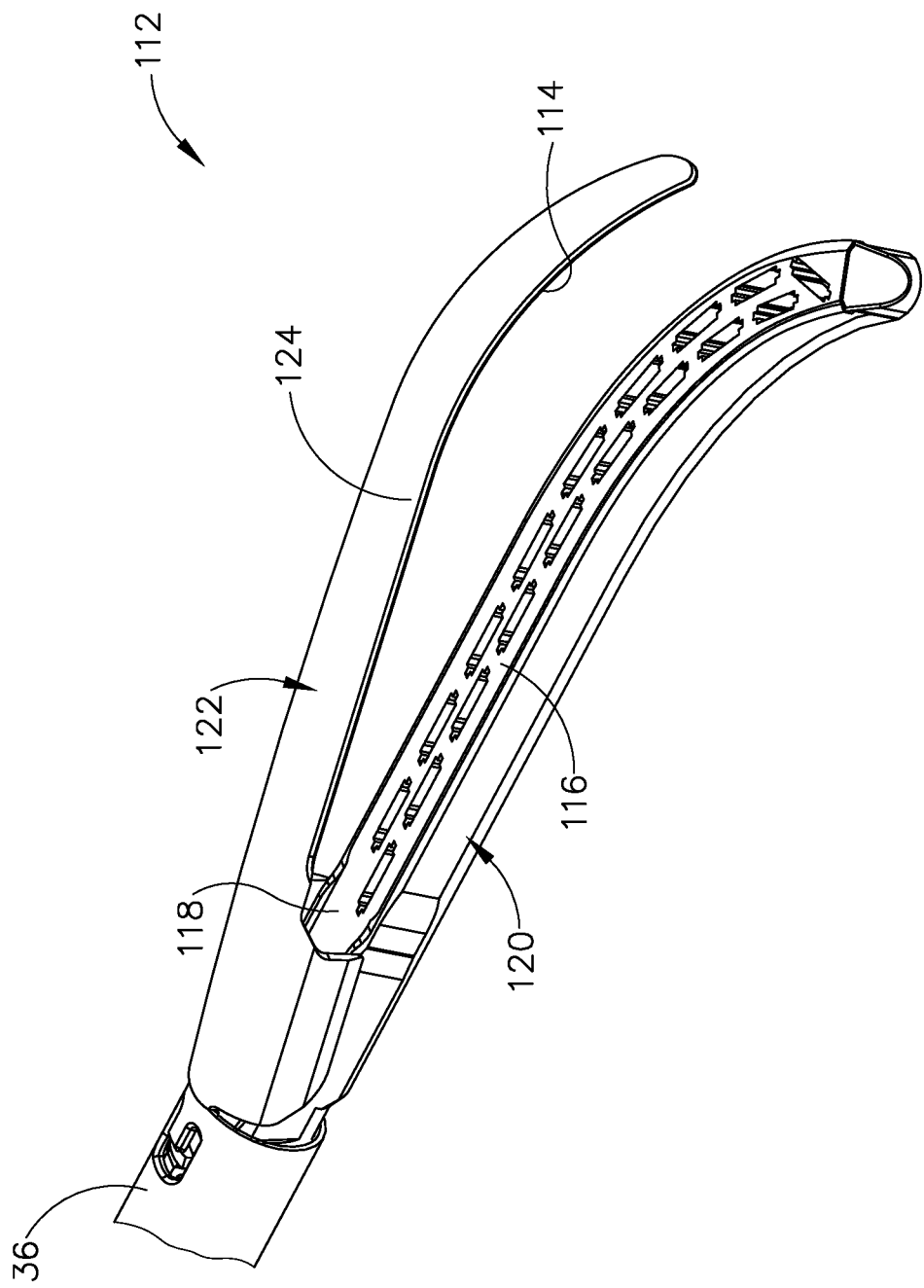
FIG. 5 depicts a perspective view of a second exemplary end effector, with the end effector in an open configuration.

FIG. 5 shows end effector (112) having upper crush surface (114), lower crush surface (116), and staple cartridge (118). Since end effector (112) may be incorporated into a variation of surgical instrument (10), it should be understood that end effector (112) may be used in conjunction with handle assembly (20) (see FIG. 1) and shaft assembly (30) (see FIG. 1) discussed above in greater detail. Except as otherwise described below, end effector (112), in conjunction with handle assembly (20) (see FIG. 1) and shaft assembly (30) (see FIG. 1), is configured and operable similar to end effector (40) (see FIG. 1).

End effector (112) of the present example further includes a lower jaw (120) and an upper jaw (122). Upper jaw (122) forms an anvil (124) and is pivotally mounted relative to lower jaw (120) for receiving the tissue therebetween. More particularly, anvil (124) is pivotable toward and away from lower jaw (120) between an open position and a closed position (e.g., in response to pivotal movement of trigger (24) (see FIG. 1) toward and away from pistol grip (22) (see FIG. 1)). This pivotable action of anvil (124) may be provided in the same manner as described above with reference to anvil (60). By way of further example only, the features for firing staples, forming staples, and severing tissue may be configured and operable in accordance with at least some of the teachings of U.S. patent application Ser. No. 14/884,272, entitled "Method of Applying Staples to Liver and Other Organs," filed Oct. 15, 2015, issued as U.S. Pat. No. 10,342,535 on Jul. 9, 2019, the disclosure of which is incorporated by reference herein.

B. Exemplary Method of Tissue Resection with a Crush Surface

FIGS. 6A-6F show one example of using end effector (112) to resect tissue, such as a liver parenchyma tissue (200), and to ligate a vessel or duct (202) therein. As noted above, vessel or duct (202) may comprise a hepatic vein or a hepatic artery. It should also be understood that the method may further include the use of end effector (112) to ligate other vessels such as the portal vein and extrahepatic vessels, etc.

Figure 6A:
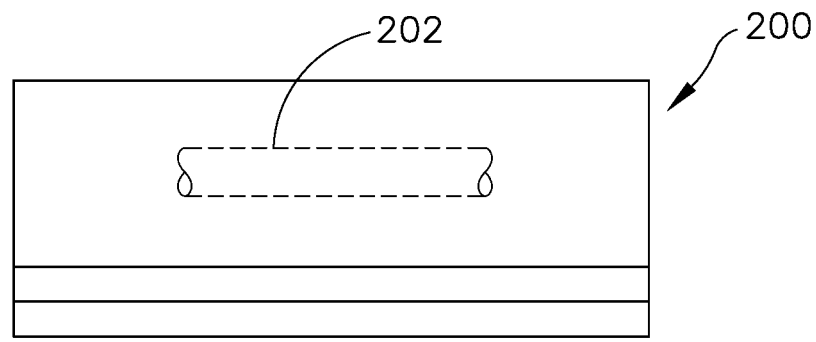
FIG. 6A depicts a schematic representation of a liver having a vessel extending through the liver tissue.
Figure 6B:
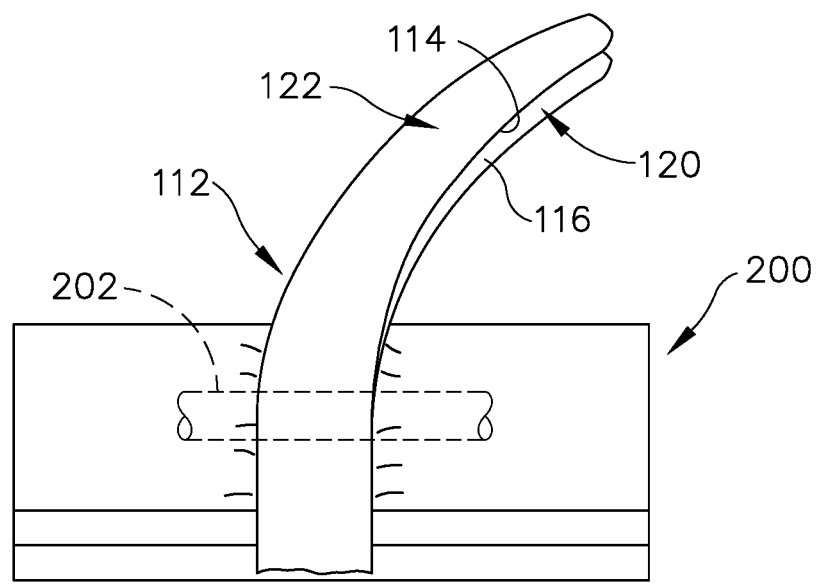
FIG. 6B depicts the schematic representation of the end effector of FIG. 5 fracturing the liver tissue of FIG. 6A without fracturing the vessel.

As shown in FIG. 6B, the operator positions end effector (112) such that tissue (200), including vessel or duct (202), is located between lower and upper jaws (120, 122). The operator then compresses tissue (200) between upper and lower crush surfaces (114, 116) of upper and lower jaws (120, 122), respectively, to deliver the predetermined crush pressure to tissue (200). By way of example only, jaws (120, 122) may be actuated in this manner by pivoting trigger (24) (see FIG. 1) toward pistol grip (22) (see FIG. 1). It should be understood that jaws (120, 122) need not necessarily be actuated to a fully closed configuration. In some instances, the operator may rely on tactile feedback through trigger (24) (see FIG. 1) and pistol grip (22) (see FIG. 1) to determine whether the operator has achieved a desired gap between jaws (120, 122) to suitably crush tissue (200) without undesirably damaging vessel or duct (202). In addition, or in the alternative, the operator may rely on visual feedback.

Figure 6C:
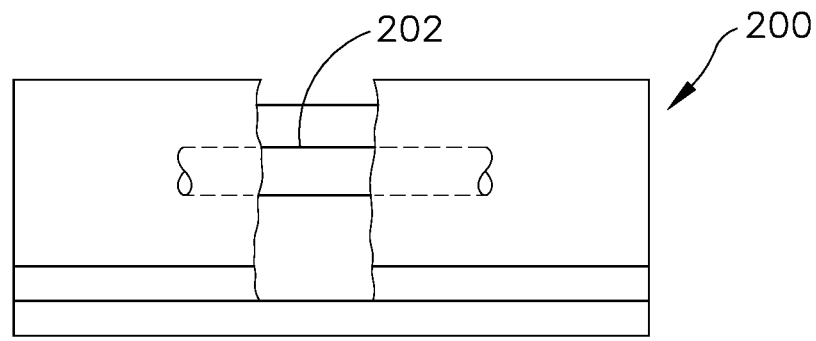
FIG. 6C depicts the schematic representation of the vessel of FIG. 6B exposed from the fractured liver tissue of FIG. 6A.

In any case, the crush pressure applied by jaws (120, 122) effectively severs tissue (200), and the operator then removes end effector (112) from tissue (200) to view whether or not any vessels or ducts (202) are present. As shown in FIG. 6C, vessel or duct (202) remains intact and is left exposed, extending between severed portions of tissue (200).

Figure 6D:
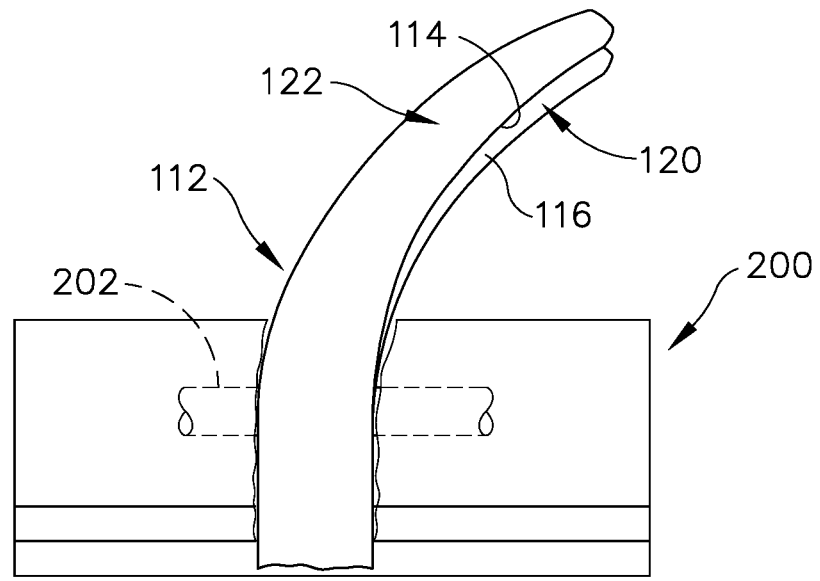
FIG. 6D depicts the schematic representation of the end effector of FIG. 5 stapling the exposed vessel of FIG. 6C.
Figure 6E:
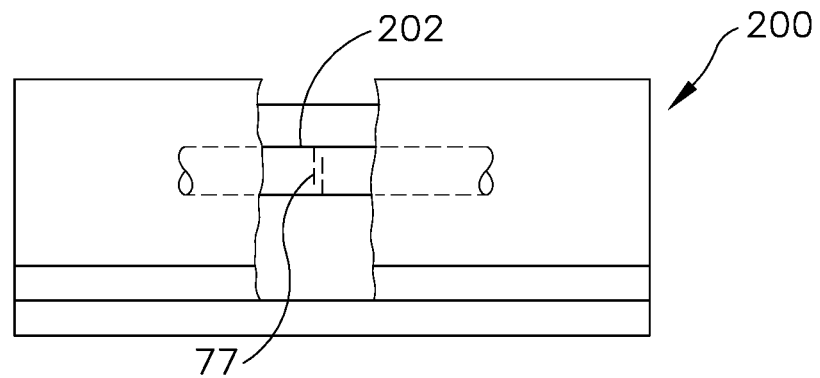
FIG. 6E depicts the schematic representation of the vessel of FIG. 6D exposed and stapled.
Figure 6F:
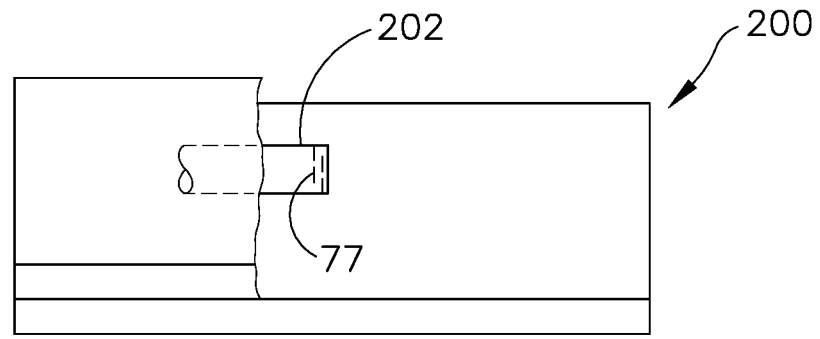
FIG. 6F depicts the schematic representation of the liver of FIG. 6A having a portion of the liver tissue and the vessel resected therefrom.

In some instances, the operator may leave vessel or duct (202) intact. However, in the present example, the operator ligates vessel or duct (202) to complete the resection of a severed portion of tissue (200), as shown in FIG. 6D and FIG. 6E. Ligation includes placement of at least some of overlapping staples (77) within vessel or duct (202) as discussed above in greater detail. It should therefore be understood that the same end effector (112) may be used to crush (and thereby sever) tissue (200) of the liver and also ligate a vessel or duct (202) in the tissue (200). In the present example, after ligation of vessel or duct (202), the operator removes end effector (112) from liver tissue (200) and severs vessel or duct (202) with another surgical instrument (not shown) known in the art for cutting tissue, such as a conventional blade or shears, etc. Thereby, the operator completes resection of a right portion of tissue (200) and the corresponding portion of the vessel or duct (202), as shown in FIG. 6F. The applied staples (77) seal a severed end (318) of the vessel or duct (202).

As described above, the operator removes end effector (112) for viewing vessel (202) as shown in FIG. 6C. Alternatively, the operator may apply the predetermined crush pressure (or as determined based on tactile and/or visual feedback as noted above), as shown in FIG. 6B, and immediately thereafter ligate any tissue remaining therein, such as the tissue of vessel or duct (202). Thus, it is not necessary to view such tissue before ligation, but the operator may find such viewing desirable in one or more liver resection procedures. It will be appreciated that the above described resection is merely illustrative and not limited to liver tissue. It should be understood that tissue resection with end effector (112) may be performed on other tissues within the patient as desired by the user.

III. EXEMPLARY SURGICAL INSTRUMENT WITH HYDRAULICALLY ACTUATED CRUSH SURFACE

While the versions of surgical instrument (10) described above provide various examples of an end effector (40, 112) that may be used to staple and sever tissue within a patient, such as by crushing and fracturing the tissue with crush surfaces (114, 116), it will be appreciated the alternative crush surfaces may be alternatively configured to sever the tissue. One such method of severing tissue may include hydraulically engaging one or more crush surfaces against the tissue to sever the tissue. Hydraulic engagement may be passive, such as by a deformable hydraulic member simply being directed against the tissue; or the hydraulic engagement may be active, such as by a deformable hydraulic member being expanded against the tissue after initially engaging the tissue. Of course, the hydraulic engagement may also be some combination of active and passive in other embodiments. It will thus be appreciated that any such structures described herein may be readily combined to achieve various manners of crushing and fracturing tissue.

As used herein, the term "deformable" refers to any shape change of the hydraulic member with fluid contained therein from a resulting pressure on the fluid. Such pressure may be passively applied by forcing tissue against the hydraulic member and thereby deforming the hydraulic member to the tissue. Pressure may also be actively applied from within the hydraulic member by introducing fluid into the hydraulic member. Furthermore, the term "contains" with respect to the fluid within the deformable hydraulic member generally refers to having fluid therein during use and broadly includes containing a predetermined amount of fluid within the deformable hydraulic member or a variable amount of fluid within the deformable hydraulic member. Accordingly, the terms "deformable" and "contains" are not intended to limit the invention described here. In some versions, the hydraulic member is formed at least in part of an extensible material. In some other versions, the hydraulic member is deformable yet non-extensible. Various suitable materials that may be used to form a hydraulic member will be apparent to those of ordinary skill in the art in view of the teachings herein End effectors (212, 312, 412, 512, 612, 712, 812) are described below in the context of dissecting liver tissue (e.g., liver parenchyma) and, in some instances, using staples to ligate associated vessels or ducts (e.g., portal vein, hepatic vein branches, hepatic artery branches, extrahepatic vessels, etc.). While the following description of end effectors (212, 312, 412, 512, 612, 712, 812) and related methods of treatment are provided in the context of liver resection, it will be appreciated that end effectors (212, 312, 412, 512, 612, 712, 812) may be alternatively configured to treat any tissue in the human body with similar features. It should also be understood that that the features discussed below may be readily incorporated into the variations of surgical instrument (10) discussed above and/or surgical instruments (210, 410, 810) discussed below. To this end, like numbers indicate like features described above in greater detail.

Figure 7:
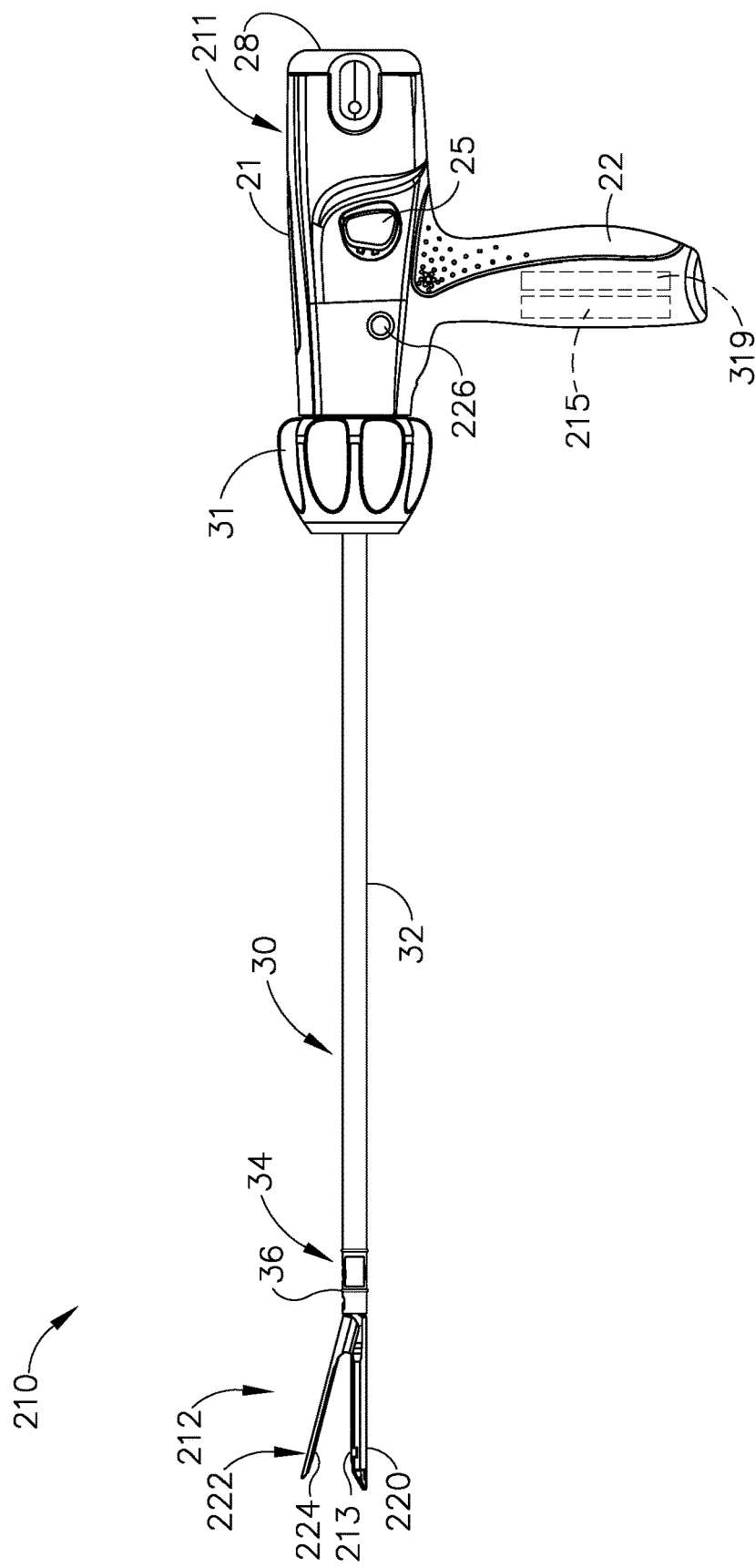
FIG. 7 depicts a side elevational view of another exemplary articulating surgical stapling instrument having a third exemplary end effector.

A. Exemplary End Effector with a Staple Cartridge Having a Central Deformable Member FIGS. 7-8 show surgical instrument (210) with a handle assembly (211), a third exemplary end effector (212), and shaft assembly (30) extending therebetween to generally support and operate end effector (212) as discussed above in greater detail. End effector (212) includes a deformable hydraulic member (213) extending longitudinally along a central portion of deck (73) between lower and upper jaws (220, 222). In the present example, deformable hydraulic member (213) is affixed to deck (73) and removably connects to end effector (212) via a fluid coupling (not shown) for replacement with staple cartridge (70). Alternatively, deformable hydraulic member (213) may be affixed to a reusable portion of end effector (212) for reuse.

Deformable hydraulic member (213) of the present example is configured to actively fracture tissue for severing a portion of tissue by receiving a fluid therein. To this end, deformable hydraulic member (213) is more particularly a deformable hydraulic balloon (213). Balloon (213) is fluidly connected to a fluid reservoir (215), which contains a fluid, such as a liquid or gas. Fluid reservoir (215) of the present example is supported within the handle assembly (211) and is fluidly connected to deformable hydraulic balloon (213) via a supply conduit (217). Alternatively, fluid reservoir (215) may be positioned in another portion of surgical instrument (210) or even exterior of surgical instrument (210). In either case, deformable hydraulic balloon (213) is configured to expand from a contracted stated to an expanded state by introducing the fluid into the deformable hydraulic balloon (213) from fluid reservoir (215). Thus, as deformable hydraulic balloon (213) expands, a crush surface (214) of deformable hydraulic balloon (213) forcibly engages the tissue and fractures the tissue against another crush surface (216) on anvil (224) as discussed below in greater detail.

In some versions, deformable hydraulic balloon (213) is operatively connected to a fluid actuator (226) on handle assembly (211) and is configured to be manipulated by the operator to selectively inflate deformable hydraulic balloon (213) toward the expanded state. Of course, it will be appreciated that other mechanisms for selectively inflating deformable hydraulic balloon (211) may alternatively be used.

Handle assembly (211) further includes one example of a pressure control system (319) that is fluidly connected to deformable hydraulic balloon (213). In some versions, more fluid from the fluid reservoir (215) than needed may be introduced into deformable hydraulic balloon (213) during expansion toward the expanded state. In fact, the excess fluid may overfill deformable hydraulic balloon (319) beyond a predetermined maximum expansion pressure. Pressure control system (319) is thus further configured to limit the expansion pressure to the predetermined maximum expansion pressure and will be discussed below with respect to FIGS. 12A-12C in greater detail.

Figure 9A:
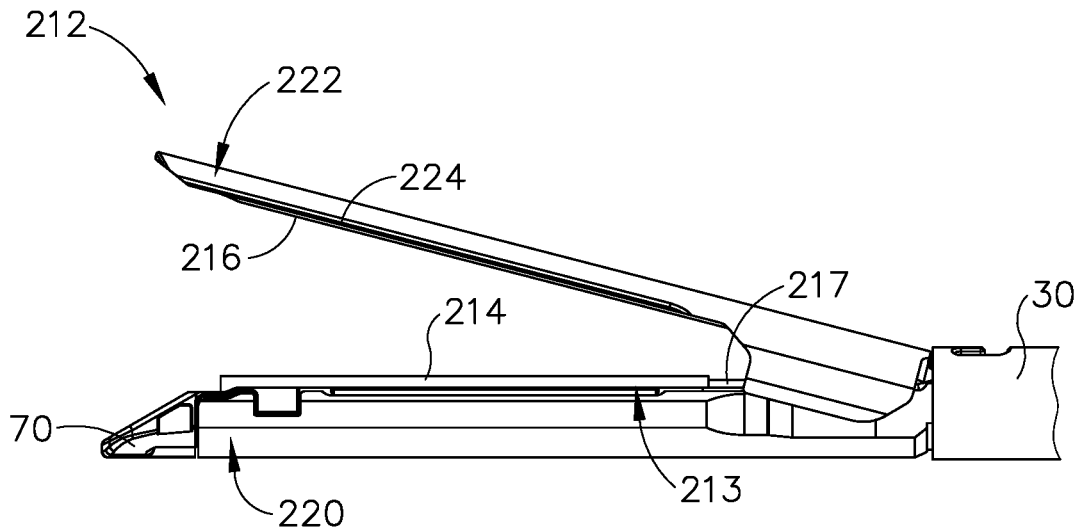
FIG. 9A depicts a side elevational view of the end effector of FIG. 8, with the end effector in the open configuration.
Figure 9B:
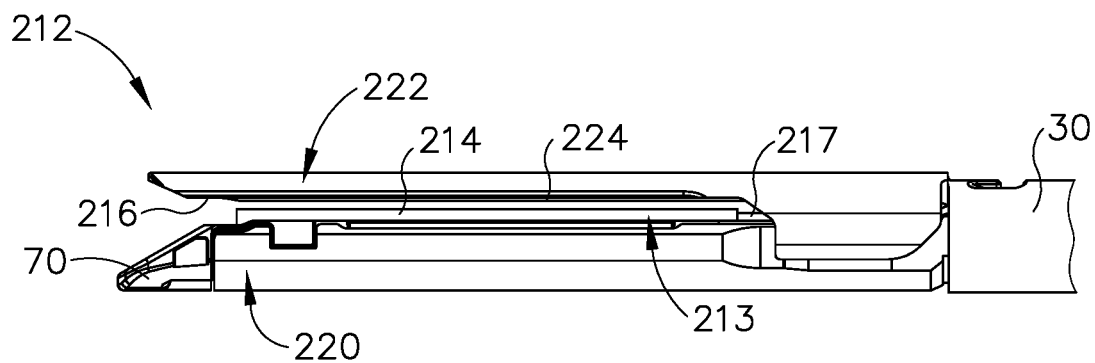
FIG. 9B depicts a side elevational view of the end effector of FIG. 8, with the end effector in a closed configuration and a deformable hydraulic member in a contracted state.
Figure 9C:
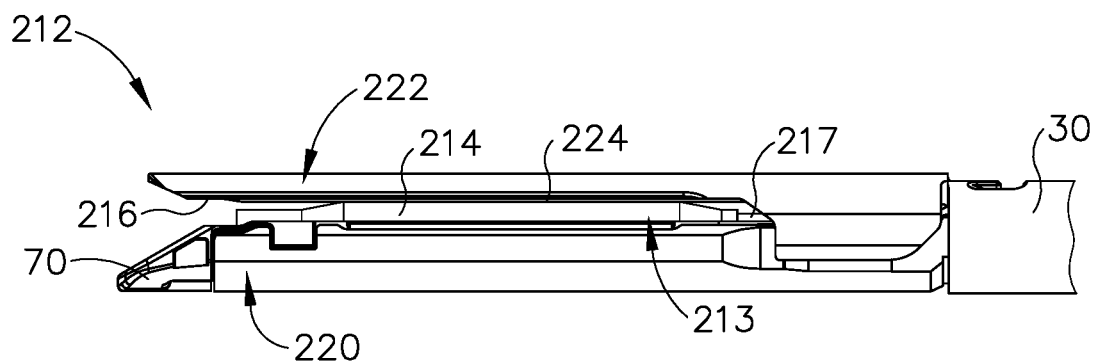
FIG. 9C depicts a side elevational view of the end effector of FIG. 8, with the end effector in the closed configuration and the deformable hydraulic member in an expanded state.

In use, FIG. 9A illustrates the lower and upper jaws (220, 222) in the open configuration and configured to receive tissue between crush surfaces (214, 216) of deformable hydraulic balloon (213) and anvil (224). Once tissue is received in the open configuration, upper jaw (222) pivots toward lower jaw (220) to the closed configuration with the tissue captured therebetween. The operator then selectively manipulates the fluid actuator (226) (see FIG. 7) to direct fluid from fluid reservoir (215) (see FIG. 7) and into the deformable hydraulic balloon (213), thereby expanding the deformable hydraulic balloon (213) from the contracted state, as shown in FIG. 9B, to the expanded state, as shown in FIG. 9C.

During this expansion of hydraulic balloon (213), the crush surface (214) on deformable hydraulic balloon (213) compresses the tissue against crush surface (216) on anvil (224). The compression continues until the tissue fractures or the pressure of the fluid, as monitored by pressure control system (319) (see FIG. 12A), reaches the predetermined maximum expansion pressure. By using a deformable surface of balloon (213) to crush the tissue instead of using two non-deformable surfaces, there may be a reduced risk of inadvertently crushing or severing the vessels or ducts (202) in the tissue. In the context of the liver or other similar tissue, after the tissue has been severed by crushing, staple cartridge (70) is fired so as ligate the vessels or ducts (202) that have been exposed as a result of the crushing (see FIG. 6F).

Figure 10:
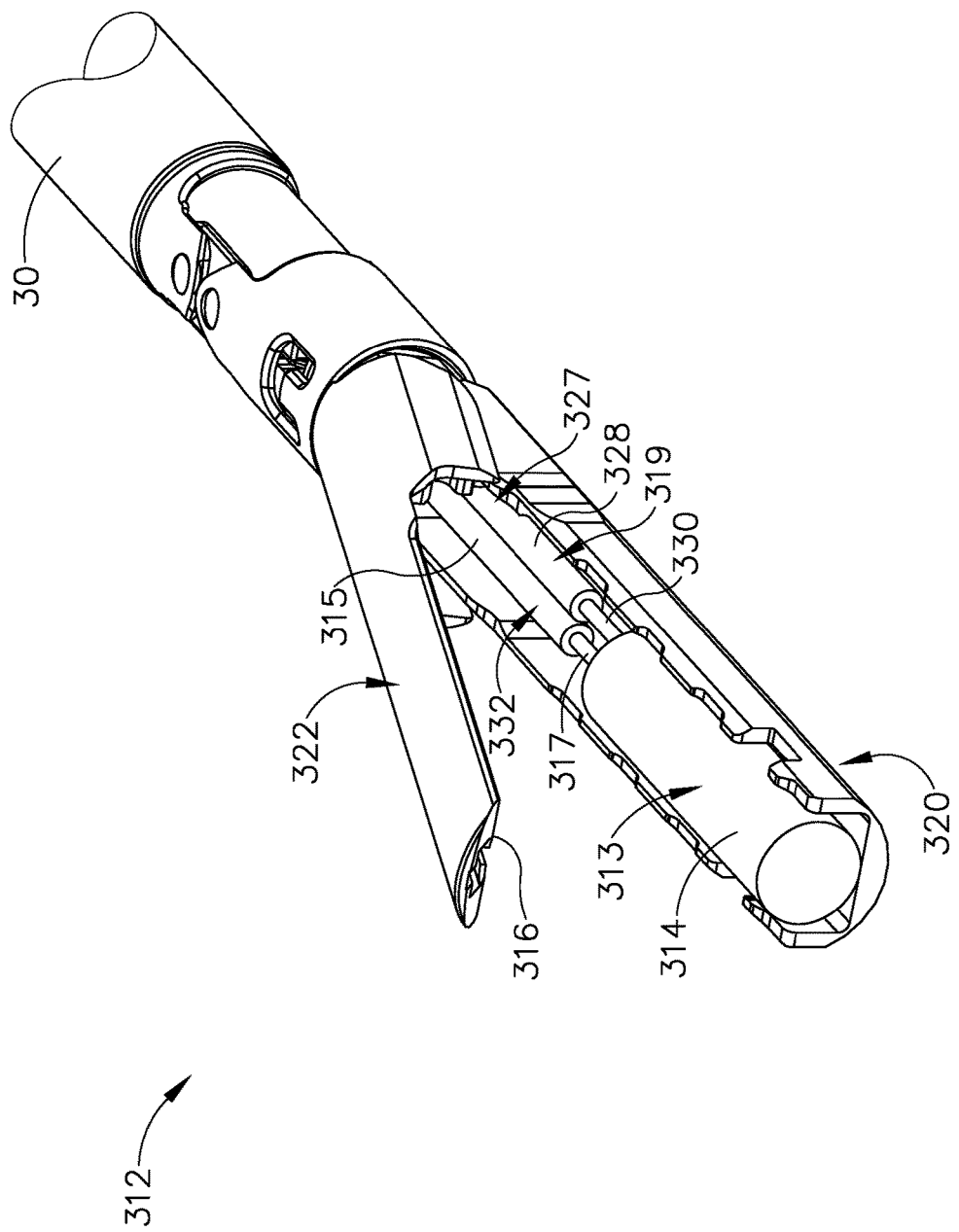
FIG. 10 depicts a perspective view of a fourth exemplary end effector, with the end effector in an open configuration.

B. Exemplary End Effector with a Central Deformable Member and a Pressure Control System FIGS. 10-11C show a fourth exemplary end effector (312) and shaft assembly (30). End effector (312) includes a deformable hydraulic member (313) extending longitudinally along a central portion of a lower jaw (320) below an upper jaw (322). Notably, end effector (312) does not include staple cartridge (70) as shown above, but may nonetheless be used for fracturing and severing tissue. In the present example, deformable hydraulic member (313) is supported by lower jaw (320) and removably connects to end effector (312) via a fluid coupling (not shown) for replacement. Alternatively, deformable hydraulic member (313) may be affixed to lower jaw (320) for reuse.

Deformable hydraulic member (313) of the present example is configured to actively fracture tissue for severing a portion of tissue by receiving a fluid in hydraulic member (313). To this end, deformable hydraulic member (313) is more particularly a deformable hydraulic balloon (313). Hydraulic balloon (313) is fluidly connected to a pump (332). Pump (332) is formed by a piston (334) and a fluid reservoir (315), which contains a fluid, such as a liquid or gas. Pump (332) of the present example is supported within lower jaw (322) of end effector (312) and is fluidly connected to deformable hydraulic balloon (313) via a supply conduit (317). Deformable hydraulic balloon (313) is configured to expand from a contracted stated to an expanded state by activating pump (332) to introduce the fluid into the deformable hydraulic balloon (313) from fluid reservoir (315). Thus, as deformable hydraulic balloon (313) expands, a crush surface (314) of deformable hydraulic balloon (313) forcibly engages the tissue and fractures the tissue against another crush surface (316) on an underside of upper jaw (322) as discussed below in greater detail. In some versions, pump (332) is operatively connected to fluid actuator (226) (see FIG. 7) on handle assembly (211) for selectively directing movement of piston (334).

End effector (312) further includes pressure control system (319) that is fluidly connected to deformable hydraulic balloon (313). As discussed above, in some versions, more fluid from fluid reservoir (315) than needed may be introduced into deformable hydraulic balloon (313) during expansion toward the expanded state beyond the predetermined maximum expansion pressure. Pressure control system (319) is thus configured to limit the expansion pressure to the predetermined maximum expansion pressure.

Pressure control system (319) of this example further includes a pressure relief reservoir (327) with a resilient body (328) that is configured to expand from a contracted state to an expanded state. Resilient body (328) is fluidly connected to deformable hydraulic balloon (313) via a relief conduit (330) for fluid communication therebetween. The resiliency of body (328) is tuned to the predetermined maximum expansion pressure such that deformable hydraulic balloon (313) generally initiates expansion under a lower pressure than resilient body (328). However, once the fluid pressure within deformable hydraulic balloon (313) increases to the predetermined maximum expansion pressure, resilient body (328) of pressure relief reservoir (327) begins to expand from its contracted state to limit pressure in deformable hydraulic balloon (313).

In the present example, body (328) is extensible and thus the extensible resilience of body (328) defines the pressure threshold at which body (328) will begin to expand. In some other versions, body (328) is non-extensible but a resilient member (e.g., leaf spring, stent-like cage, etc.) is engaged with body; and the resilience of the resilient member defines the pressure threshold at which body (328) will begin to expand. Other suitable ways in which resilient body (328) may be configured to only expand after the fluid pressure reaches a predetermined threshold value will be apparent to those of ordinary skill in the art in view of the teachings herein. It should also be understood that one or more pressure sensitive valves (e.g., interposed between relief conduit (330), supply conduit (317), and/or pressure relief reservoir (327)) may be used to establish a threshold fluid pressure value to selectively provide pressure relief to deformable hydraulic balloon (313). Pressure relief reservoir (327) is thus not intended to be unnecessarily limited to the example described herein.

It should be understood from the foregoing that, in the event that additional fluid flow from fluid reservoir (315) or additional downward pressure is applied to deformable hydraulic balloon (313), resilient body (328) will expand to maintain the pressure of the predetermined maximum expansion pressure within deformable hydraulic balloon (313). In the event that forces acting on deformable hydraulic balloon (313) reduce decrease after expansion of pressure relief reservoir (327), resilient body (328) contracts to maintain the predetermined maximum expansion pressure until resilient body (328) returns to the contracted state. Once resilient body (328) returns to the contracted state, the expansion pressure of deformable hydraulic balloon (313) may then decrease below the predetermined maximum expansion pressure. Pressure relief reservoir (327) is thus configured to limit the expansion pressure of deformable hydraulic balloon (313) to less than or equal to the predetermined maximum expansion pressure to inhibit damaging the tissue, such as vessel or ducts (202) (see FIGS. 6A-6F).

Figure 11A:
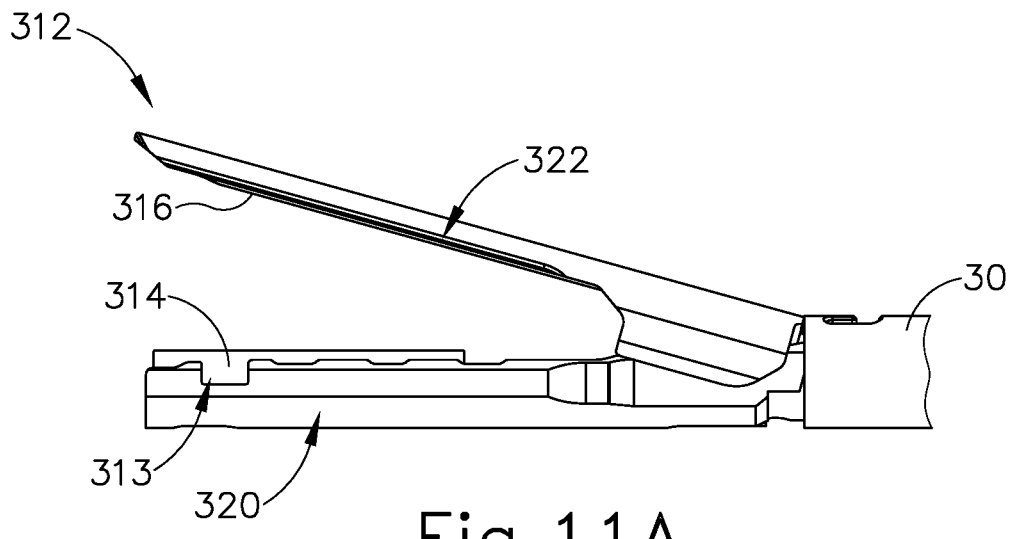
FIG. 11A depicts a side elevational view of the end effector of FIG. 10, with the end effector in the open configuration.
Figure 11B:
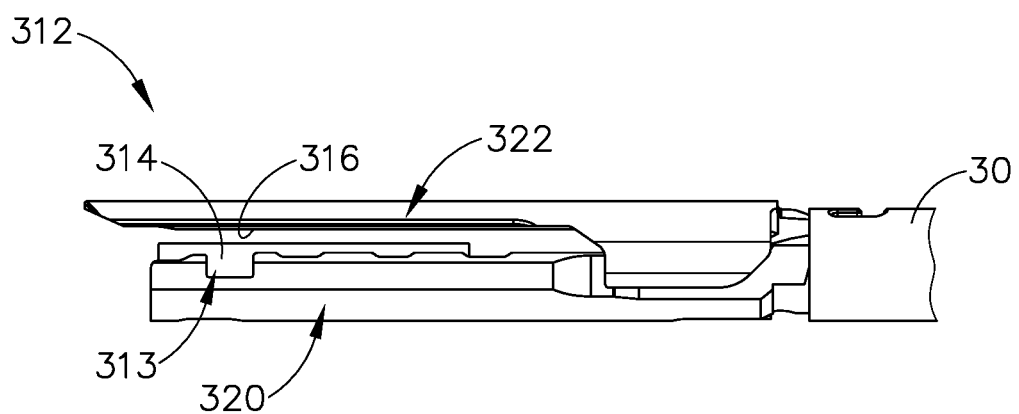
FIG. 11B depicts a side elevational view of the end effector of FIG. 10, with the end effector in a closed configuration and a deformable hydraulic member in a contracted state.
Figure 11C:
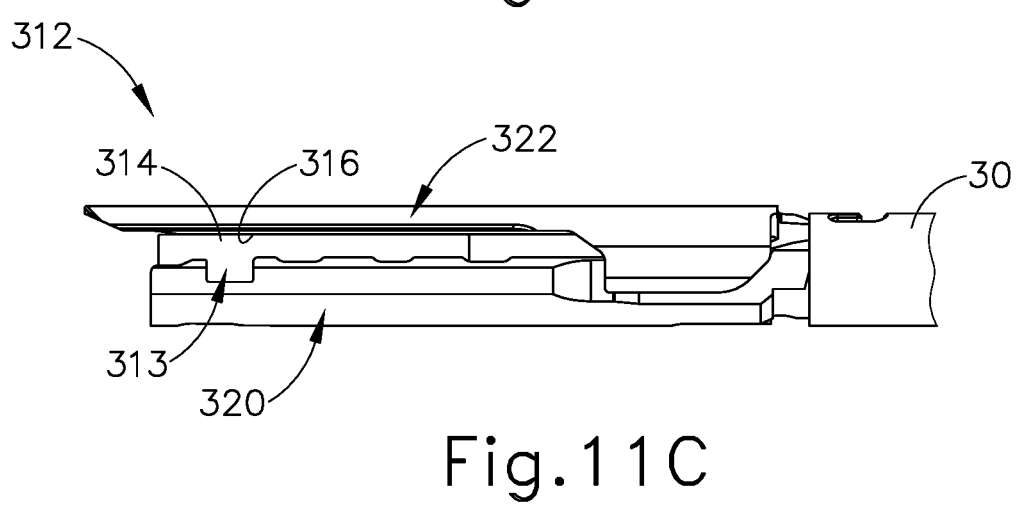
FIG. 11C depicts a side elevational view of the end effector of FIG. 10, with the end effector in the closed configuration and the deformable hydraulic member in an expanded state.

In use, FIG. 11A shows the lower and upper jaws (320, 322) in the open configuration to receive tissue between crush surfaces (314, 316) of deformable hydraulic balloon (313) and upper jaw (322). Once tissue is received in the open configuration, upper jaw (322) pivots toward lower jaw (320) to the closed configuration with the tissue captured therebetween. The operator then selectively manipulates the fluid actuator (226) (see FIG. 7) to direct fluid from fluid reservoir (315) (see FIG. 10) and into the deformable hydraulic balloon (313), thereby expanding the deformable hydraulic balloon (313) from the contracted state, as shown in FIG. 11B, to the expanded state, as shown in FIG. 11C.

Figure 12A:
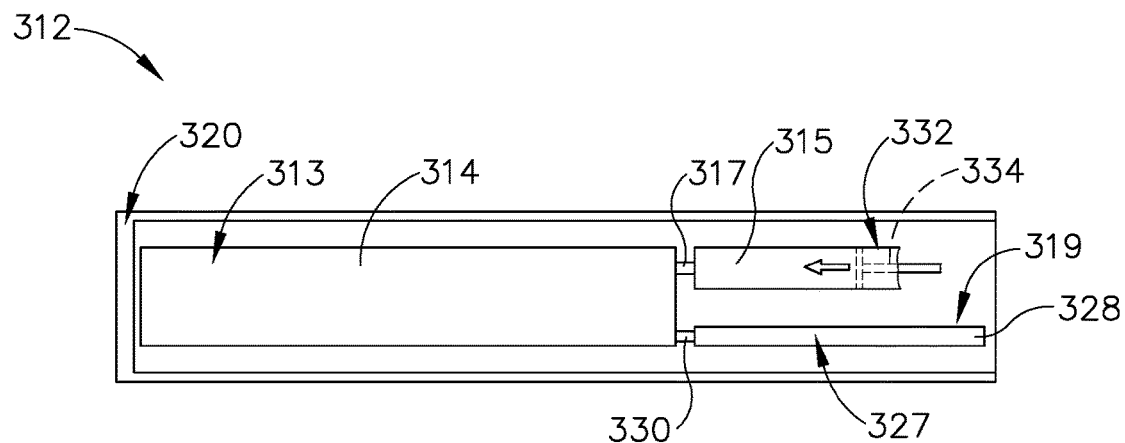
FIG. 12A depicts a top view of a lower jaw of the end effector of FIG. 10 with the deformable hydraulic member in the contracted state and a mechanical pressure regulator.
Figure 12B:
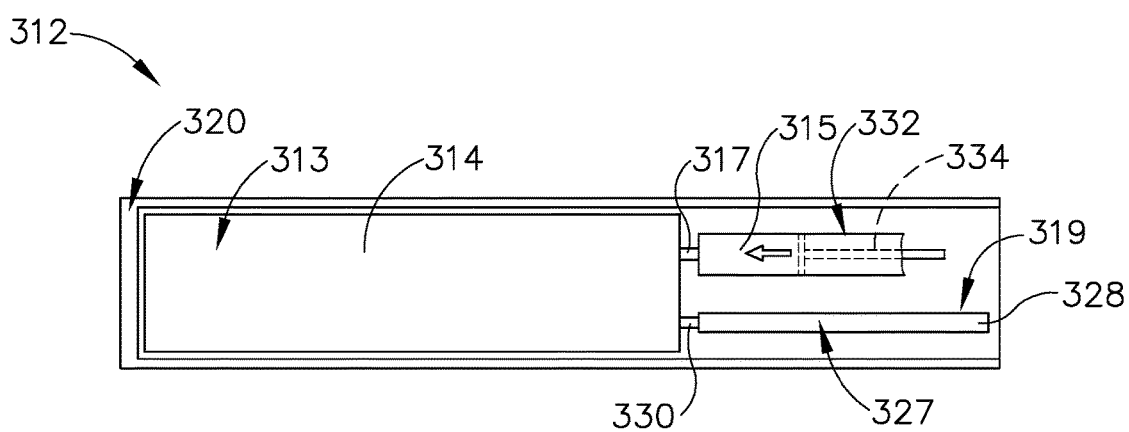
FIG. 12B depicts a top view of a lower jaw of the end effector of FIG. 10 with the deformable hydraulic member expanding toward the expanded state.
Figure 12C:
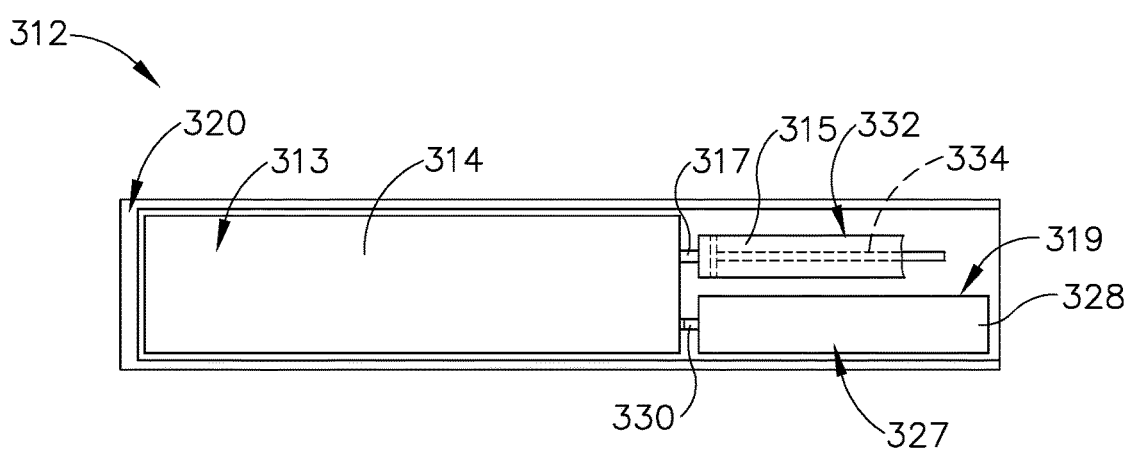
FIG. 12C depicts a top view of a lower jaw of the end effector of FIG. 10 with the deformable hydraulic member in the expanded state.

During this expansion, crush surface (314) on the deformable hydraulic balloon (313) compresses the tissue against the crush surface (316) on the upper jaw (322). With respect to FIGS. 12A-12C, the compression continues until the tissue fractures or the pressure of the fluid, as monitored by the pressure control system (319) (see FIG. 12A), reaches the predetermined maximum expansion pressure. By way of example, fluid actuator (219) (see FIG. 7) is a portion of a fluid delivery system (322), which also includes a piston (334) within fluid reservoir (315) that forcibly directs the fluid into deformable hydraulic balloon (313) as shown in FIGS. 12A-12B. Once the fluid pressure within deformable hydraulic balloon (313) results in the predetermined maximum expansion pressure, resilient body (328) expands to receive fluid from deformable hydraulic balloon (313) as shown in FIG. 12C. Thereby, pressure relief system (319) maintains the fluid pressure at or below the predetermined maximum expansion pressure until the fluid from fluid reservoir (315) is fully discharged.

In the foregoing example, end effector (312) includes a combination of pump (332) and pressure relief system (319). However, it should be understood that these two features do not necessarily need to be used in combination. For instance, some variations of end effector (312) may simply include pump (332), to provide active expansion of balloon (313), without also including pressure relief system (319). As yet another merely illustrative alternative, some variations may include pressure relief system (319) without also including pump (332). It should therefore be understood that some passive versions of balloon (313) (e.g., like balloon (213)) may be used with a pressure relief system (319). In any case, and as noted above with respect to end effector (212), the deformability of balloon (313) may provide a reduced risk of inadvertently crushing or severing the vessels or ducts (202) in the tissue. In other words, a deformable crush surface provided by balloon (313) may be less likely to inadvertently crush or sever a vessel or duct (202) as compared with a non-deformable crush surface. This effect may be further enhanced in versions where a pressure relief system (319) is included. It should therefore be understood that pressure relief system (319) may be tuned to provide pressure relief when fluid pressures reach a level that is just below a pressure level associated with crushing of vessels or ducts (202).

Figure 13A:
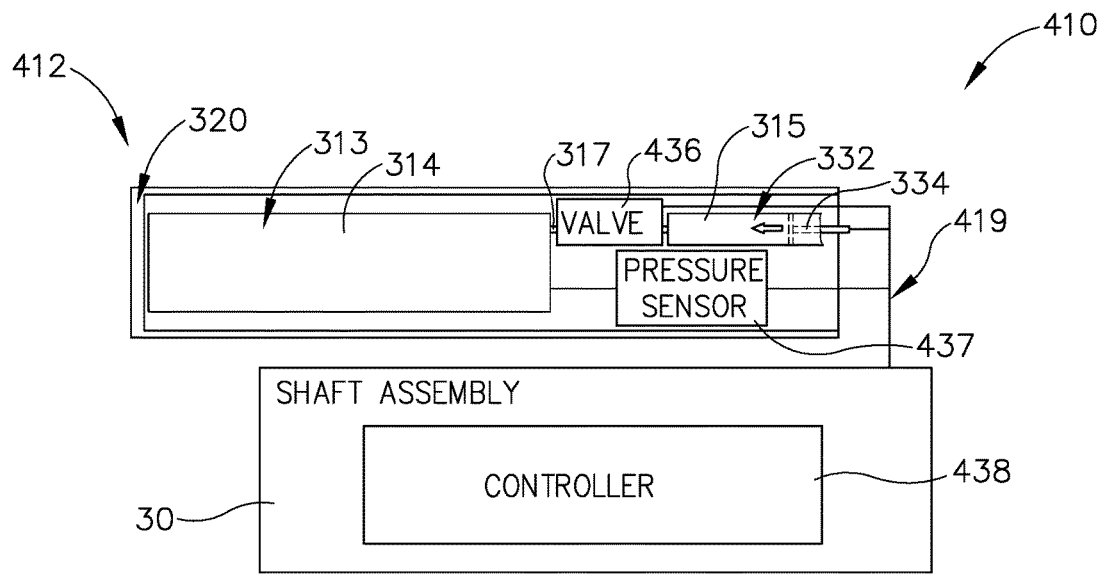
FIG. 13A depicts a schematic top view of a fifth exemplary end effector with a lower jaw having a deformable hydraulic member in a contracted state and an electromechanical pressure regulator.
Figure 13B:
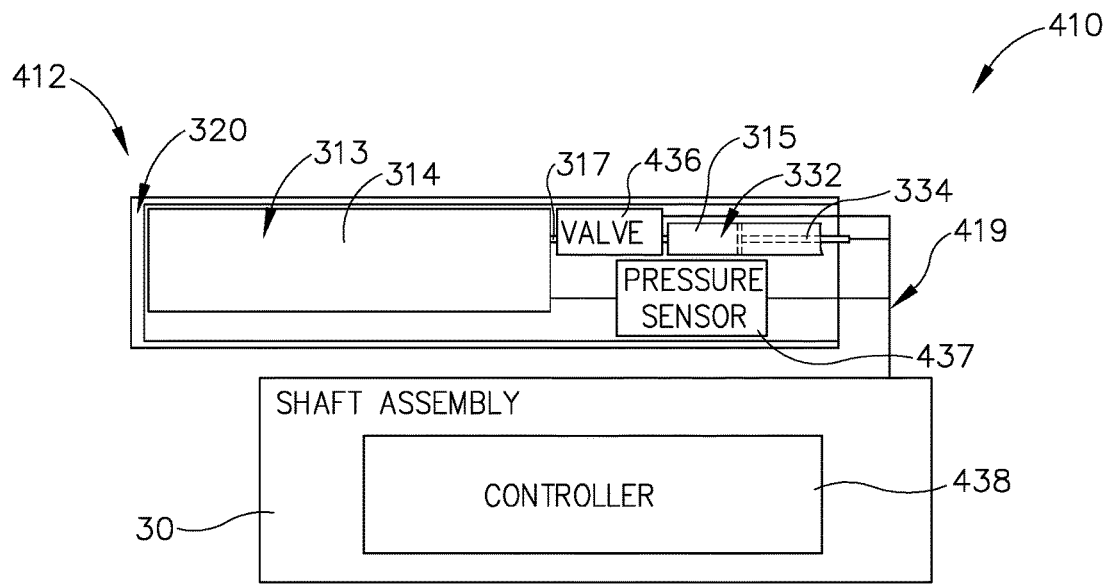
FIG. 13B depicts the schematic top view of the end effector of FIG. 13A, with the deformable hydraulic member in an expanded state.

FIGS. 13A-13B illustrate another exemplary surgical instrument (410) having a fifth exemplary end effector (412) connected to shaft assembly (30) and an alternative pressure control system (419). Pressure control system (419) includes a valve (436), a pressure sensor (437), and a controller (438), such as a microcontroller. Valve (436) is fluidly connected between fluid reservoir (315) and deformable hydraulic balloon (313). Pressure sensor (437) is operatively connected to deformable hydraulic balloon (313) and is configured to measure the fluid pressure therein. Controller (438) is operatively connected to each of valve (436), piston (334), and pressure sensor (437) for directing the fluid via pump (332), monitoring the pressure within the deformable hydraulic balloon (313), and halting the flow of additional fluid once deformable hydraulic balloon (313) reaches the predetermined maximum expansion pressure.

Figure 14A:
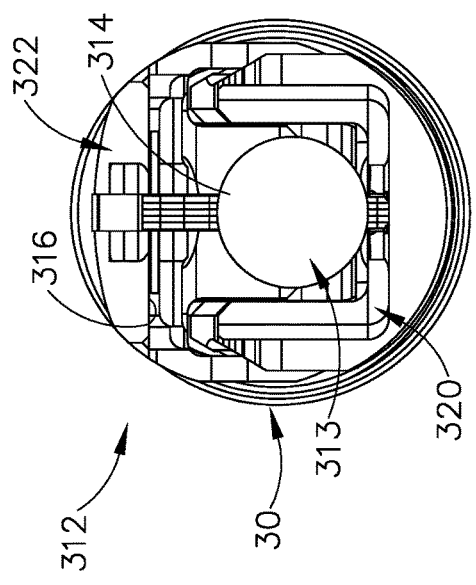
FIG. 14A depicts a distal end elevational view of the end effector of FIG. 10 with the deformable hydraulic member in the contracted state.
Figure 14B:
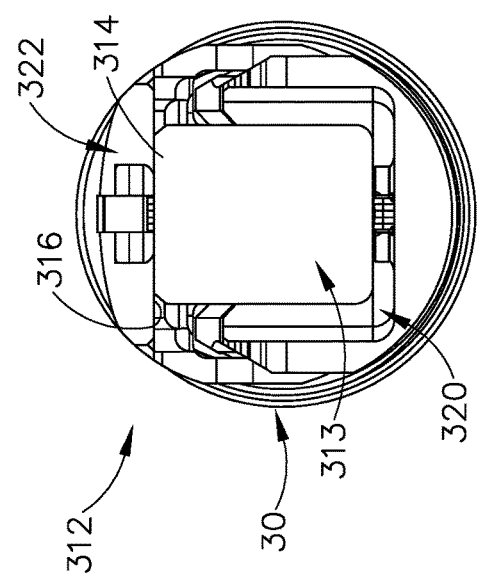
FIG. 14B depicts a distal end elevational view of the end effector of FIG. 10 with the deformable hydraulic member in the expanded state.

In use, valve (436) is initially open such that piston (334) forces the fluid into deformable hydraulic balloon (313) for expansion. While monitoring the fluid pressure within deformable hydraulic balloon (313), controller (438) continues to actuate pump (332) to thereby direct the fluid into deformable hydraulic balloon (313) via open valve (436). Once the fluid pressure reaches the predetermined maximum expansion pressure, controller (438) directs piston (334) to halt further fluid flow and closes valve (436) in order to inhibit the fluid pressure from exceeding the predetermined maximum expansion pressure. In the event that additional force, such as from the tissue, engages deformable hydraulic balloon (313) while fracturing the tissue, controller (438) may further open valve (436) and retract piston (334). Thereby, fluid is removed from deformable hydraulic balloon (313) until the fluid pressure therein reduces to the predetermined maximum expansion pressure. Pressure control system (419) is thus configured to add and/or remove fluid by monitoring fluid pressure while in the contracted and expanded states respectively shown in FIGS. 14A-14B.

Figure 15:
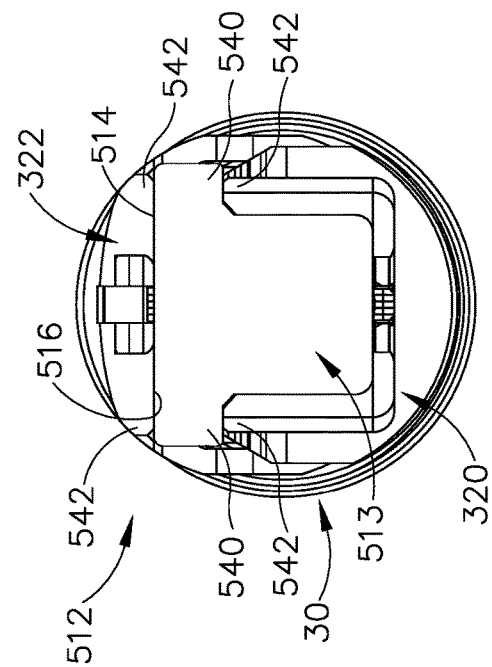
FIG. 15 depicts a distal end elevational view of a sixth exemplary end effector with a deformable hydraulic member in an expanded state.

C. Exemplary End Effector with a Central Deformable Member Including a Lateral Edge Lip FIG. 15 shows a fifth exemplary end effector (512) configured to actively crush tissue when expanded from the contracted state to an expanded state. End effector (512) generally operates as other end effectors described herein, but includes a deformable hydraulic balloon (513) having a pair of lateral edge lips (540) for an enlarged crush surface (514). More particularly, deformable hydraulic balloon (513) in the expanded state is generally T-shaped and includes the pair of lateral edge lips (540) extending respectively outwardly along each lateral edge (542) that longitudinally extends along lower jaw (320). Lateral edge lips (540) cover lateral edges (542) to increase the surface area of crush surface (514) and inhibit tissue from directly contacting lateral edges (542). In some exemplary uses, such lateral edge lip (540) may thereby reduce the amount of damage to tissue that may otherwise occur from the tissue directly contacting the relatively rigid and non-deformable lateral edges (542).

D. Exemplary End Effector with a Pair of Central Deformable Members

Figure 16A:
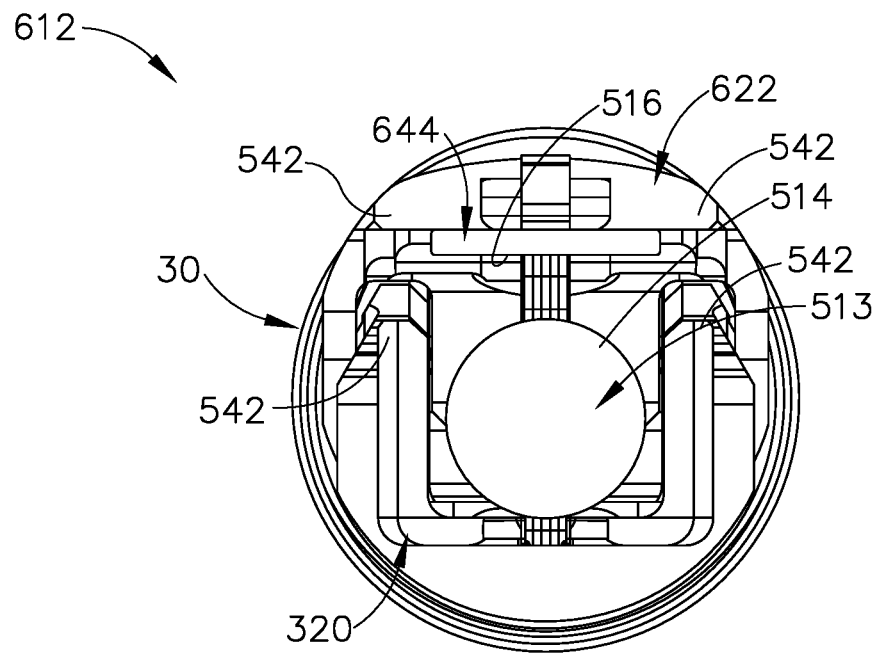
FIG. 16A depicts a distal end elevational view of a seventh exemplary end effector with an upper deformable hydraulic member in a contracted state and a lower deformable hydraulic member in a contracted state.
Figure 16B:
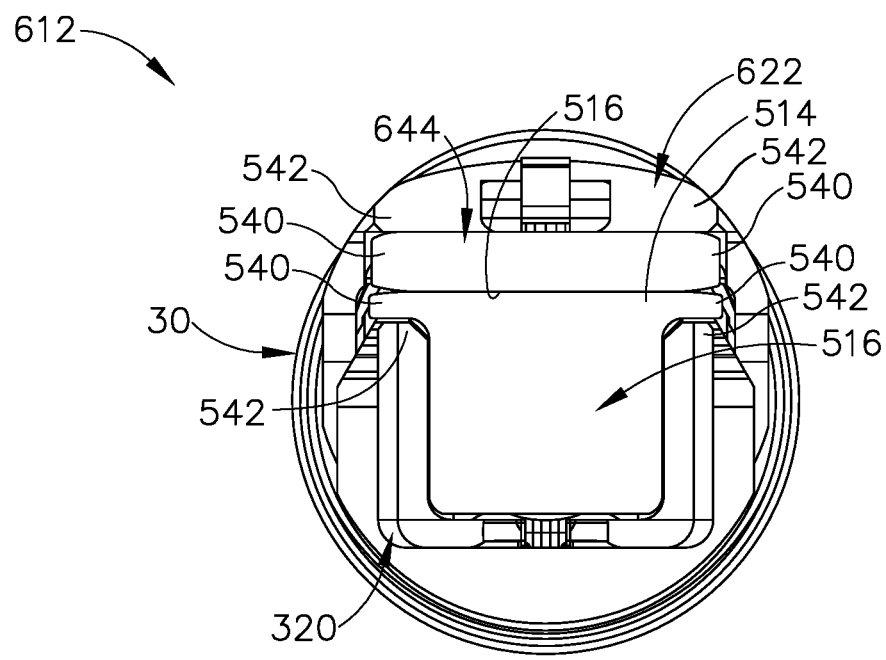
FIG. 16B depicts a distal end elevational view of the end effector of FIG. 16A, with the upper and lower facture balloons in an expanded state.

FIGS. 16A-16B show a seventh exemplary end effector (612) with deformable hydraulic balloon (513) for operation as discussed above. In addition, end effector (612) also includes another deformable hydraulic member (644), which is in the form of another deformable hydraulic balloon (644), that extends longitudinally along an underside of an upper jaw (622). Deformable hydraulic balloon (644) includes crush surface (516), which is configured to cooperate with crush surface (514) to fracture tissue therebetween.

In use, the tissue is captured between lower and upper jaws (320, 622) in the closed configuration. The user manipulates fluid actuator (226) (see FIG. 7) thereby causing the pair of lower and upper deformable hydraulic balloons (513, 644) to simultaneously expand from the contacted state toward the expanded state. Crush surfaces (514, 516) thereby compress the tissue therebetween in order to fracture the tissue for severing a portion of the tissue. Alternatively, lower and upper deformable hydraulic balloons (513, 644) may be independently expandable and/or one of the lower and upper deformable hydraulic balloons (513, 644) may be expandable before and/or after the other depending on use. The invention is thus not intended to be unnecessarily limited to simultaneous expansion.

In another example, deformable hydraulic balloons (513, 644) may be replaced with one or more passive deformable hydraulic members that simply contain a predetermined amount of fluid without such contracted and expanded states. In other words, the passive deformable hydraulic members do not receive fluid nor discharge fluid therefrom, but simply retain the fluid contained therein and deform to the tissue in compression. In use, the operator simply moves lower and upper jaws (320, 322, 622) toward the closed configuration and, in doing so, fractures the tissue between crush surfaces (514, 516). It will be appreciated that any deformable hydraulic members discussed herein may be configured for active expansion or passive state uses. In versions where balloons (513, 644) are passive, balloons (513, 644) may be fluidly isolated from each other or in fluid communication with each other. In versions where balloons (513, 644) are passive and in fluid communication with each other, fluid from one balloon (513, 644) may be transferred to the other balloon (513, 644) as balloons (513, 644) bear against tissue to crush the tissue. This may enable balloons (513, 644) to each have a substantially equal fluid pressure.

By way of further example, lower and upper jaws (320, 622) may be closed about tissue while balloons (513, 644) are in a non-expanded state. Thus, in this closed configuration jaws (320, 622) may define a gap therebetween to receive the tissue. Balloons (513, 644) may then be expanded while jaws (320, 622) maintain the closed configuration. Accordingly, actively expanding deformable hydraulic balloons (513, 644) from the contracted state to the expanded state may, in whole or in part, traverse the gap to fracture the tissue. In contrast, passive deformable hydraulic members may similarly define a gap in the closed configuration that is small enough to fracture the tissue without expansion.

Figure 17:
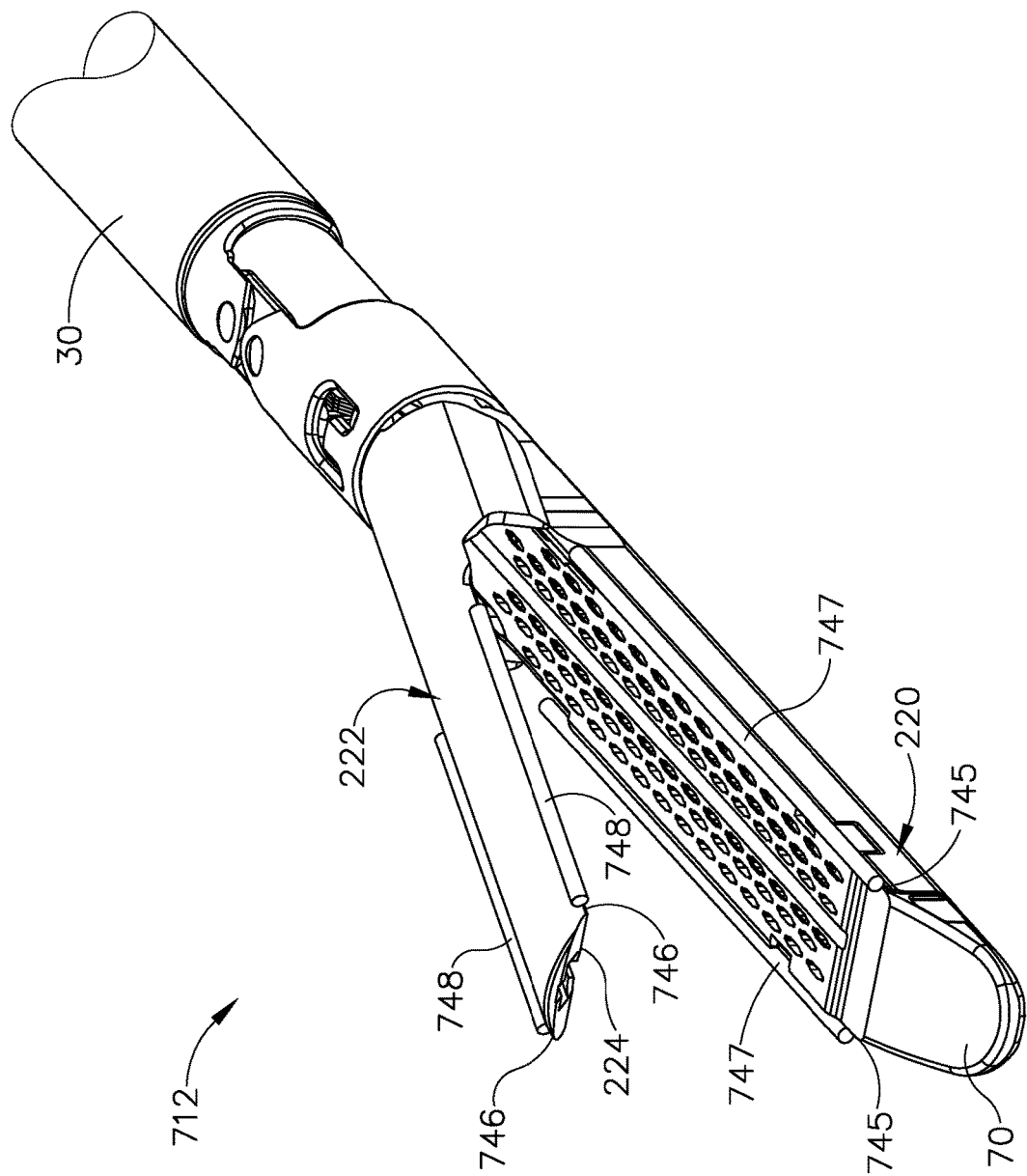
FIG. 17 depicts a perspective view of an eighth exemplary end effector, with the end effector in an open configuration and having a pair of upper deformable hydraulic members and a pair of lower deformable hydraulic members.

E. Exemplary End Effector with a Pair of Upper Lateral Deformable Members and a Pair of Lower Lateral Deformable Members FIG. 17 shows an eighth exemplary end effector (712) extending from shaft assembly (30) with replaceable staple cartridge (70). End effector (712) includes lower jaw (220) with a pair of longitudinally extending lower lateral edges (745) and upper jaw (222) with a pair of longitudinally extending upper lateral edges (746). In order to fracture tissue and inhibit tissue from directly contacting lateral edges (745, 746), end effector (712) further includes a pair of lower deformable hydraulic members (747) and a pair of upper deformable hydraulic members (748). In some active versions, lower and upper deformable hydraulic members (747, 748) are deformable hydraulic balloons configured to expand from a contracted state toward an expanded state for fracturing the tissue and covering the lateral edges (745, 746). It will be appreciated that such lower and upper deformable hydraulic balloons (747, 748) may operatively inflated and maintained as discussed above with respect to other balloons discussed herein. In some passive versions, lower and upper deformable hydraulic members (747, 748) retain a predetermined amount of fluid respectively in each member (747, 748) for crushing tissue without transitioning between contracted and expanded states.

Figure 18A:
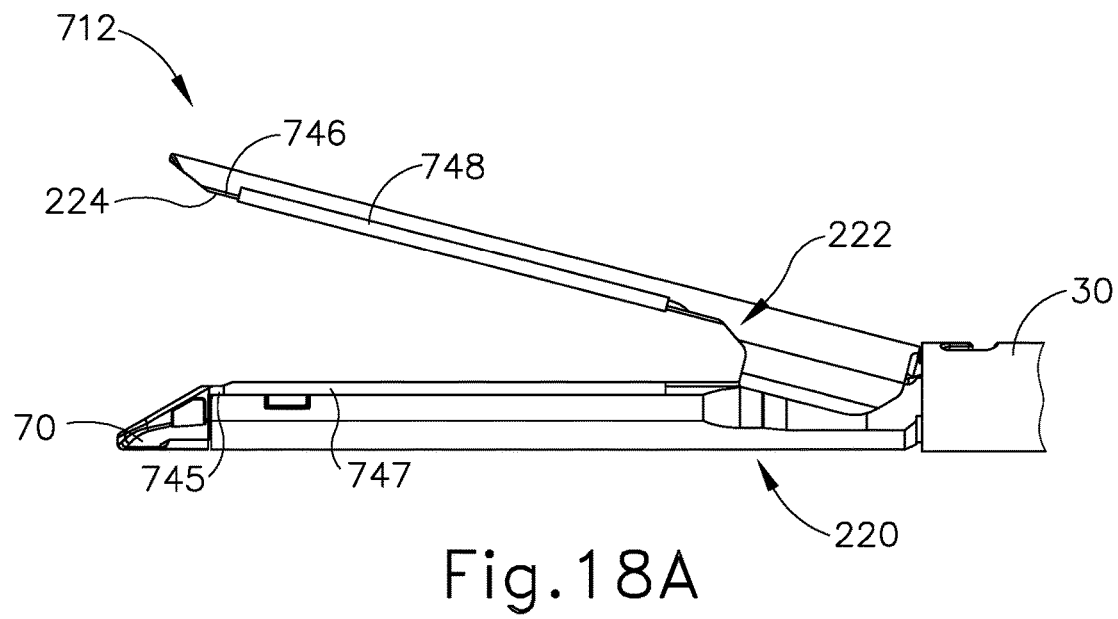
FIG. 18A depicts a side elevational view of the end effector of FIG. 17 in the open configuration.
Figure 18B:
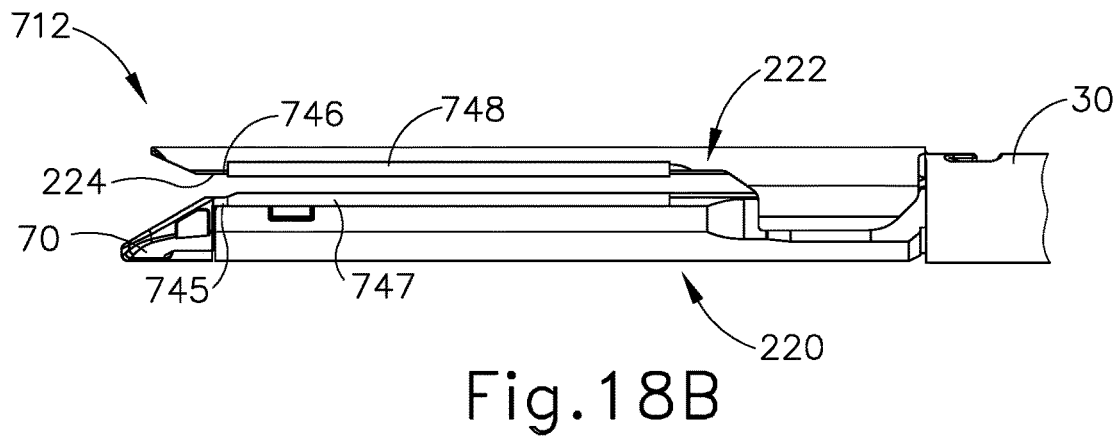
FIG. 18B depicts a side elevational view of the end effector of FIG. 17, with the end effector in a closed configuration and the pairs of upper and lower deformable hydraulic members in a contracted state.
Figure 18C:
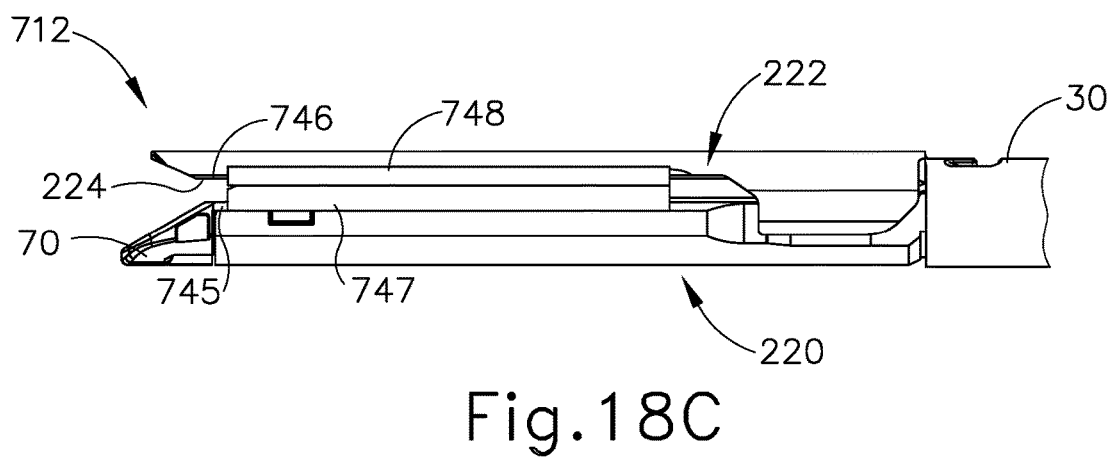
FIG. 18C depicts a side elevational view of the end effector of FIG. 17, with the end effector in the closed configuration and the pairs of upper and lower deformable hydraulic members in an expanded state.

In use as shown in FIGS. 18A-18B, lower and upper jaws (220, 222) in the open configuration and configured to receive tissue between crush surfaces (714, 716) of lower and upper deformable hydraulic balloons (747, 748). Once tissue is received in the open configuration, upper jaw (222) pivots toward lower jaw (220) to the closed configuration with the tissue captured therebetween. The operator then selectively manipulates the fluid actuator (226) (see FIG. 7) to direct fluid from fluid reservoir (215) (see FIG. 7) and into lower and upper deformable hydraulic balloons (747, 748), thereby expanding lower and upper deformable hydraulic balloons (747, 748) from the contracted state, as shown in FIG. 18B to the expanded state, as shown in FIG. 18C.

Figure 19A:
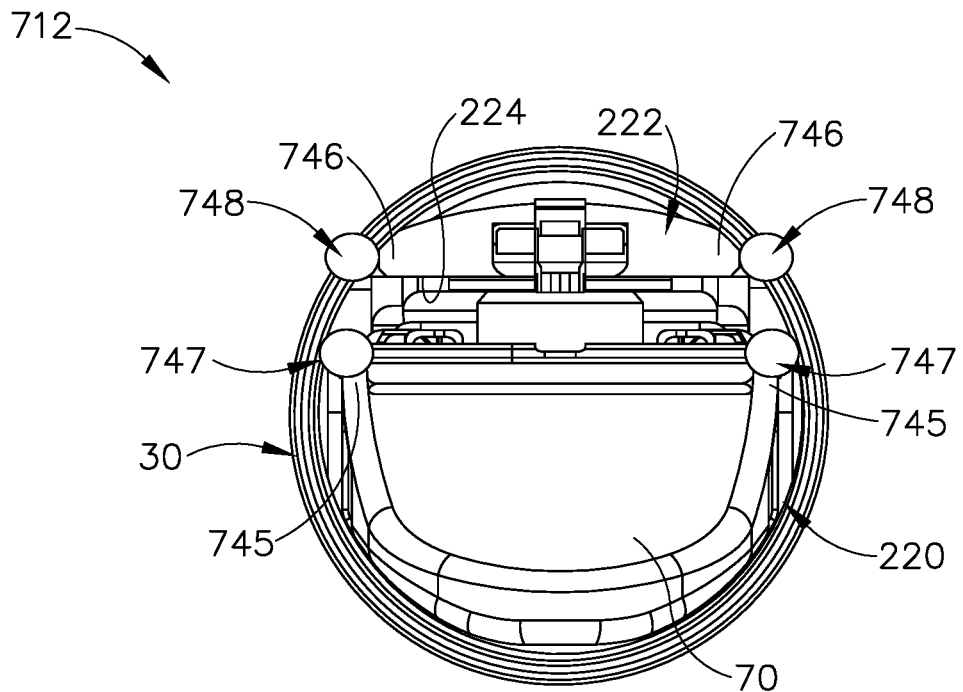
FIG. 19A depicts a distal end elevational view of the end effector of FIG. 17, with the end effector in the closed configuration and the pairs of upper and lower deformable hydraulic members in the contracted state.
Figure 19B:
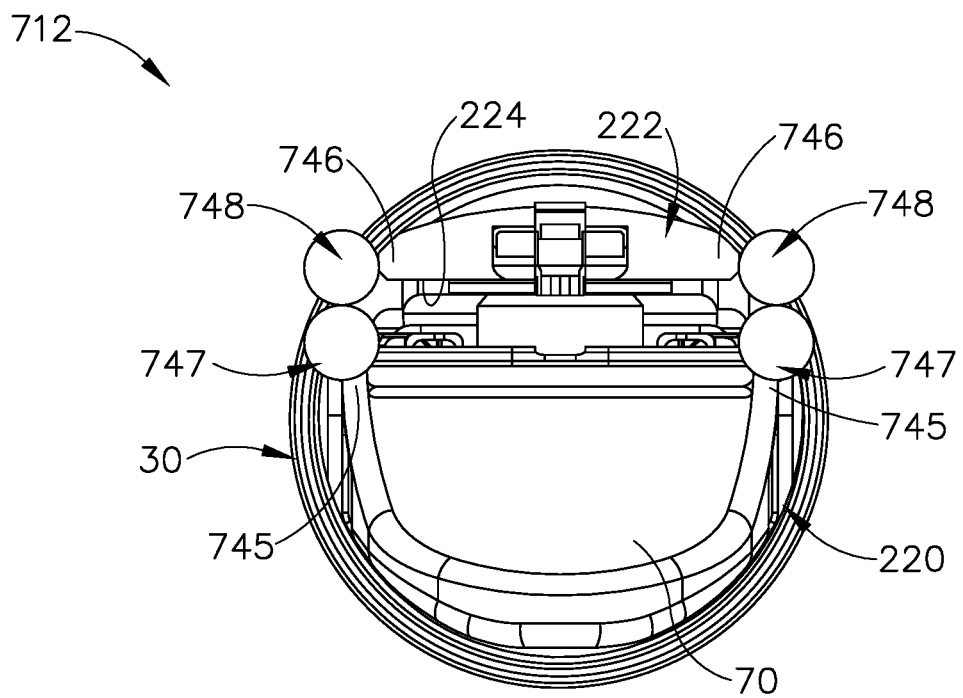
FIG. 19B depicts a distal end elevational view of the end effector of FIG. 17, with the end effector in the closed configuration and the pairs of upper and lower deformable hydraulic members in the expanded state.

During this expansion as shown in FIGS. 19A-19B, lower and upper crush surfaces (714, 716) on lower and upper deformable hydraulic balloons (747, 748) respectively compress the tissue therebetween. Lower and upper deformable hydraulic balloons (747, 748) also atraumatically urge tissue away from lower and upper lateral edges (745, 746) to inhibit unintended damage to the tissue during the operation. The compression continues until the tissue fractures or the pressure of the fluid, as monitored by the pressure control system (319) (see FIG. 12A), reaches the predetermined maximum expansion pressure. In the context of the liver or other similar tissue, staple cartridge (70) is fired so as ligate and transect the vessels or ducts (202) (see FIG. 6F).

Figure 20:
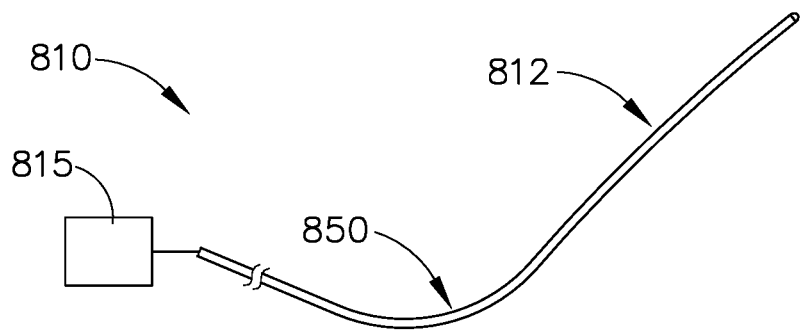
FIG. 20 depicts a side elevational view of an exemplary surgical instrument having a ninth exemplary end effector with a deformable hydraulic member.
Figure 21A:
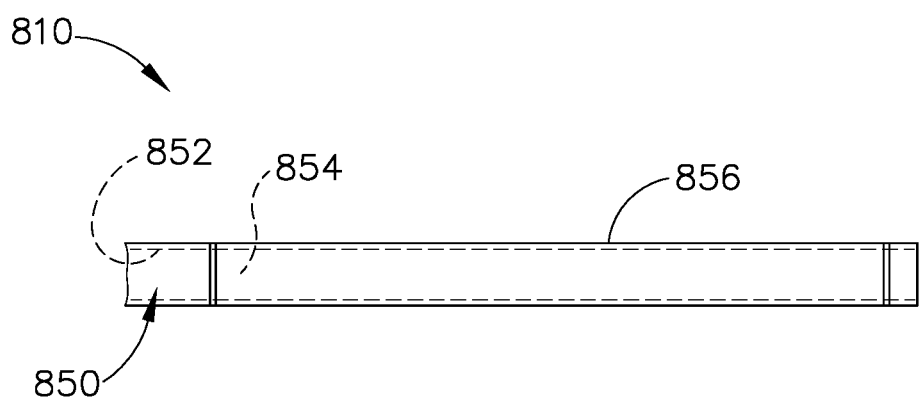
FIG. 21A depicts an enlarged side elevation view of the deformable hydraulic member of FIG. 20 in a contracted state.
Figure 21B:
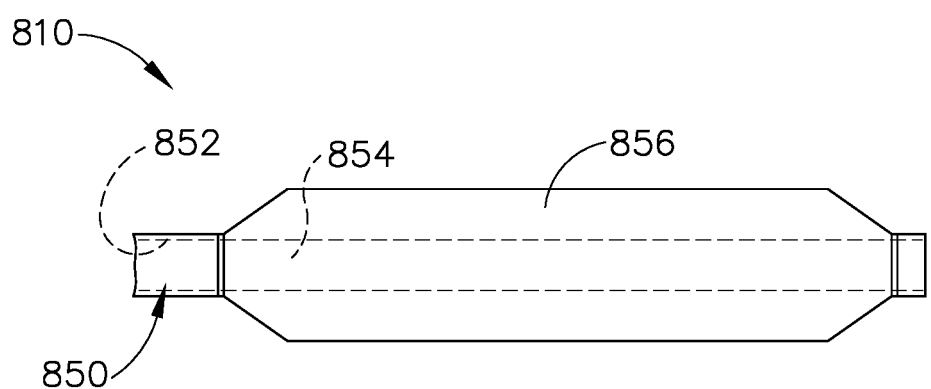
FIG. 21B depicts an enlarged side elevation view of the deformable hydraulic member of FIG. 20 in an expanded state.

F. Exemplary End Effector with a Deformable Member for Tissue Insertion Fracturing FIGS. 20-21B show yet another exemplary surgical instrument (810) having an end effector (812) including a deformable hydraulic member in the form of a hydraulic catheter (850). Hydraulic catheter (850) includes a central tube (852) defining a lumen (854) extending therethrough. Lumen (854) is configured to receive a guidewire (not shown) for directing the location of the hydraulic catheter (850) in use. In addition, or in the alternative, hydraulic catheter (850) may be guided by a guide catheter and/or any other suitable guide feature(s). It should therefore be understood that lumen (854) and a corresponding guidewire are merely optional.

Hydraulic catheter (850) further includes a deformable hydraulic balloon (856). Fluid is stored within a fluid reservoir (815), which is fluidly connected to deformable hydraulic balloon (856). Fluid reservoir (815) is configured to supply the fluid to the deformable hydraulic balloon (856) to expand the deformable hydraulic balloon from the contracted state shown in FIG. 21A toward the expanded state shown in FIG. 21B.

Figure 22A:
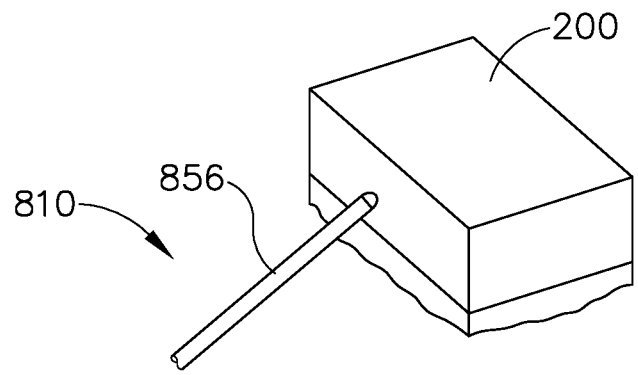
FIG. 22A depicts a schematic representation of a liver and the deformable hydraulic member of FIG. 20.
Figure 22B:
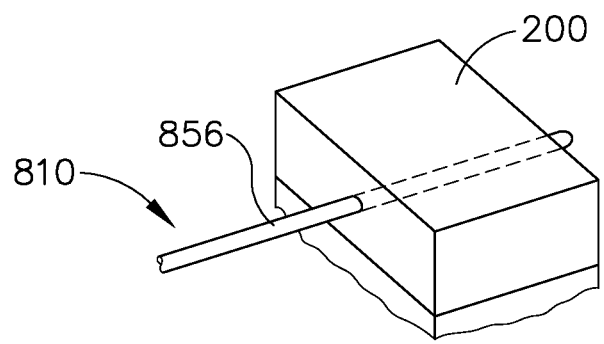
FIG. 22B depicts the schematic representation of the liver of FIG. 22A, with the deformable hydraulic member of FIG. 20 inserted into the liver in the contracted state.
Figure 22C:
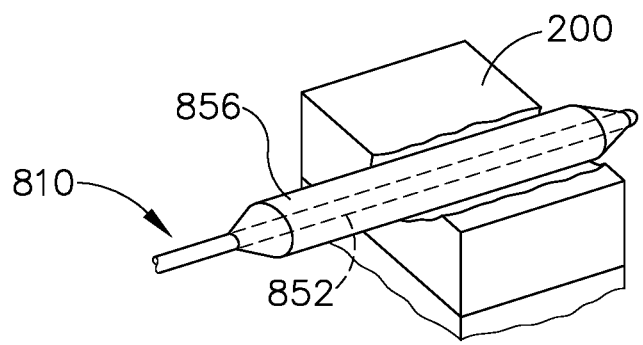
FIG. 22C depicts the schematic representation of the liver of FIG. 22A, with the deformable hydraulic member of FIG. 20 inserted into the liver in an expanded state, thereby fracturing a portion of the liver tissue.

In use, the operator inserts the guidewire (not shown) into the tissue to the location in which the operator desires to position deformable hydraulic balloon (856) as shown in FIG. 22A. Alternatively, the operator achieves the positioning as shown in FIG. 22A using a guide catheter and/or some other guide feature. Once hydraulic balloon (856) suitably positioned, and as shown in FIG. 22B, the operator inserts deformable hydraulic balloon (856) into the tissue (and along the guidewire, if a guidewire is used). Once deformable hydraulic balloon (856) is in the desirable position, the operator directs the fluid from fluid reservoir (815) and into deformable hydraulic balloon (856). In turn, the deformable hydraulic balloon (856) expands from the contracted state to the expanded state and fractures the tissue to sever the portion of the tissue shown in FIG. 22C.

IV. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument, comprising: (a) a shaft assembly; and (b) an end effector extending in a longitudinal direction from the shaft assembly, the end effector comprising: (i) a first jaw, (ii) a second jaw movably mounted relative to the first jaw and configured to transition between an open configuration and a closed configuration such that the first and second jaws are configured to have tissue positioned therebetween in the closed configuration, and (iii) a first deformable hydraulic member extending longitudinally and positioned adjacent to at least one of the first and second jaws, wherein the first deformable hydraulic member is configured to contain a fluid, wherein the first deformable hydraulic member with the fluid contained therein is configured to fracture the tissue positioned between the first and second jaws in the closed configuration.

Example 2

The surgical instrument of Example 1, wherein the first deformable hydraulic member extends longitudinally between the first and second jaws in the closed configuration.

Example 3

The surgical instrument of any one or more of Examples 1 through 2, wherein the first deformable hydraulic member contains the fluid.

Example 4

The surgical instrument of Example 3, wherein the first deformable hydraulic member extends along the first jaw.

Example 5

The surgical instrument of Example 4, wherein the end effector further includes a second deformable hydraulic member extending longitudinally along the second jaw, wherein the second deformable hydraulic member contains the fluid, and wherein the first and second deformable members are configured to fracture the tissue therebetween in the closed configuration.

Example 6

The surgical instrument of any one or more of Examples 4 through 5, wherein the first jaw includes a longitudinally extending edge, and wherein the first deformable hydraulic member is positioned along at least a portion of the edge.

Example 7

The surgical instrument of any one or more of Examples 3 through 6, further comprising a staple cartridge received within the first jaw, the staple cartridge comprising: (i) a deck facing the second jaw, (ii) a plurality of staple openings formed through the deck, and (iii) a plurality of staples positioned respectively within the plurality of staple openings, wherein the first deformable hydraulic member extends longitudinally along the deck

Example 8

The surgical instrument of any one or more of Examples 1 through 7, wherein the first deformable hydraulic member is configured to expand from a contracted state to an expanded state, and wherein the first deformable hydraulic member is configured to fracture the tissue positioned between the first and second jaws as the expandable member expands from the contracted state to the expanded state.

Example 9

The surgical instrument of Example 8, wherein the first deformable hydraulic member extends along the first jaw.

Example 10

The surgical instrument of Example 9, wherein the end effector further includes a second deformable hydraulic member extending longitudinally along the second jaw, wherein the second deformable hydraulic member is configured to contain the fluid, and wherein the first and second deformable members are configured to fracture the tissue therebetween in the closed configuration as the first deformable hydraulic member expands from the contracted state to the expanded state.

Example 11

The surgical instrument of Example 10, wherein the second deformable member is configured to expand from the contracted state to the expanded state, and wherein the first and second deformable members are configured to fracture the tissue therebetween in the closed configuration as the first and second deformable hydraulic members expand from the contracted state to the expanded state.

Example 12

The surgical instrument of any one or more of Examples 9 through 11, wherein the first jaw includes a longitudinally extending edge, and wherein the first deformable hydraulic member is positioned along at least a portion of the edge.

Example 13

The surgical instrument of any one or more of Examples 8 through 12, further comprising a staple cartridge received within the first jaw, the staple cartridge comprising: (i) a deck facing the second jaw, (ii) a plurality of staple openings formed through the deck, and (iii) a plurality of staples positioned respectively within the plurality of staple openings, wherein the first deformable hydraulic member extends longitudinally along the deck.

Example 14

The surgical instrument of any one or more of Examples 8 through 13, further comprising a pressure control system comprising: (i) a fluid actuator configured to direct the fluid into the first deformable member in order to expand the first deformable member from the contracted state to the expanded state, (ii) a pressure sensor operatively connected to the first deformable member and configured to sense a measured pressure within the first deformable member, and (iii) a controller operatively connected to the fluid actuator and the pressure sensor, wherein the controller is configured to monitor the measured pressure within the first deformable member via the pressure sensor and cease direction of the fluid into the first deformable member via the fluid actuator when the measure pressure increases to a maximum predetermined pressure.

Example 15

The surgical instrument of any one or more of Examples 1 through 14, wherein the end effector further includes a pressure relief reservoir fluidly connected to the first deformable member, wherein the first deformable member is configured to contain the fluid up to a maximum predetermined pressure, and wherein an excess pressure greater than the maximum predetermined pressure is configured to direct the fluid from the first deformable member to the pressure relief reservoir such that the deformable member and the pressure relief reservoir are configured to maintain the pressure within the first deformable member to be equal to or less than the maximum predetermined pressure.

Example 16

A staple cartridge, comprising: (a) a deck; (b) a plurality of staple openings formed through the deck; (c) a plurality of staples positioned respectively within the plurality of staple openings; and (d) a deformable hydraulic member positioned along the deck and configured to contain a fluid therein, wherein the first deformable hydraulic member with the fluid contained therein is configured to fracture tissue.

Example 17

The surgical instrument of Example 16, wherein the first deformable hydraulic member is configured to expand from a contracted state to an expanded state upon receiving the fluid therein.

Example 18

A method of operating on a tissue with a deformable hydraulic member configured to contain a fluid, the method comprising directing the deformable hydraulic member against a portion of the tissue thereby fracturing the portion of the tissue for severing the tissue.

Example 19

The method of Example 18, further comprising expanding the deformable hydraulic member from a contracted state to an expanded state.

Example 20

The method of Example 19, wherein the tissue is a liver parenchyma tissue, and the method further includes inserting the deformable hydraulic member into the liver parenchyma tissue.

V. MISCELLANEOUS

It should be understood that any one or more of the teachings, expressions, embodiments, examples, etc.

described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pub. No. 2013/0012957, entitled "Automated End Effector Component Reloading System for Use with a Robotic System, published Jan. 10, 2013, issued as U.S. Pat. No. 8,844,789 on Sep. 30, 2014, the disclosure of which is incorporated by reference herein; U.S. Pub. No. 2012/0199630, entitled "Robotically-Controlled Surgical Instrument with Force-Feedback Capabilities," published Aug. 9, 2012, issued as U.S. Pat. No. 8,820,605 on Sep. 2, 2014, the disclosure of which is incorporated by reference herein; U.S. Pub. No. 2012/0132450, entitled "Shiftable Drive Interface for Robotically-Controlled Surgical Tool," published May 31, 2012, issued as U.S. Pat. No. 8,616,431 on Dec. 31, 2013, the disclosure of which is incorporated by reference herein; U.S. Pub. No. 2012/0199633, entitled "Surgical Stapling Instruments with Cam-Driven Staple Deployment Arrangements," published Aug. 9, 2012, issued as U.S. Pat. No. 8,573,461 on Nov. 5, 2013, the disclosure of which is incorporated by reference herein; U.S. Pub. No. 2012/0199631, entitled "Robotically-Controlled Motorized Surgical End Effector System with Rotary Actuated Closure Systems Having Variable Actuation Speeds," published Aug. 9, 2012, issued as U.S. Pat. No. 8,602,288 on Dec. 10, 2013, the disclosure of which is incorporated by reference herein; U.S. Pub. No. 2012/0199632, entitled "Robotically-Controlled Surgical Instrument with Selectively Articulatable End Effector," published Aug. 9, 2012, issued as U.S. Pat. No. 9,301,759 on Apr. 5, 2016, the disclosure of which is incorporated by reference herein; U.S. Pub. No. 2012/0203247, entitled "Robotically-Controlled Surgical End Effector System," published Aug. 9, 2012, issued as U.S. Pat. No. 8,783,541 on Jul. 22, 2014, the disclosure of which is incorporated by reference herein; U.S. Pub. No. 2012/0211546, entitled "Drive Interface for Operably Coupling a Manipulatable Surgical Tool to a Robot," published Aug. 23, 2012, issued as U.S. Pat. No. 8,479,969 on Jul. 9, 2014; U.S. Pub. No. 2012/0138660, entitled "Robotically-Controlled Cable-Based Surgical End Effectors," published Jun. 7, 2012, issued as U.S. Pat. No. 8,800,838 on Aug. 12, 2014, the disclosure of which is incorporated by reference herein; and/or U.S. Pub. No. 2012/0205421, entitled "Robotically-Controlled Surgical End Effector System with Rotary Actuated Closure Systems," published Aug. 16, 2012, issued as U.S. Pat. No. 8,573,465 on Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument, comprising:
   (a) a shaft assembly; and
   (b) an end effector extending in a longitudinal direction from the shaft assembly, the end effector comprising:
      (i) a first jaw,
      (ii) a second jaw movably mounted relative to the first jaw and configured to transition in a transverse direction from an open configuration toward a closed configuration such that the first and second jaws are configured to have tissue positioned transversely therebetween in the closed configuration, and
      (iii) a first deformable hydraulic member extending longitudinally and configured to expand to an expanded state, wherein at least a portion of the first deformable hydraulic member transversely aligns with at least one of the first and second jaws to extend transversely over the at least one of the first and second jaws in the expanded state, wherein the first deformable hydraulic member is configured to contain a fluid,
   wherein the first deformable hydraulic member with the fluid contained therein is configured to fracture the tissue positioned between the first and second jaws in the closed configuration.

2. The surgical instrument of claim 1, wherein the first deformable hydraulic member extends longitudinally between the first and second jaws in the closed configuration.

3. The surgical instrument of claim 1, wherein the first deformable hydraulic member contains the fluid.

4. The surgical instrument of claim 3, wherein the first deformable hydraulic member extends along the first jaw.

5. The surgical instrument of claim 4, wherein the end effector further includes a second deformable hydraulic member extending longitudinally along the second jaw, wherein the second deformable hydraulic member contains the fluid, and wherein the first and second deformable members are configured to fracture the tissue therebetween in the closed configuration.

6. The surgical instrument of claim 3, further comprising a staple cartridge received within the first jaw, the staple cartridge comprising:
   (i) a deck facing the second jaw,
   (ii) a plurality of staple openings formed through the deck, and
   (iii) a plurality of staples positioned respectively within the plurality of staple openings,
   wherein the first deformable hydraulic member extends longitudinally along the deck.

7. The surgical instrument of claim 1, wherein the first deformable hydraulic member is configured to expand from a contracted state to the expanded state, and wherein the first deformable hydraulic member is configured to fracture the tissue positioned between the first and second jaws as the expandable member expands from the contracted state to the expanded state.

8. The surgical instrument of claim 7, wherein the first deformable hydraulic member extends along the first jaw.

9. The surgical instrument of claim 8, wherein the end effector further includes a second deformable hydraulic member extending longitudinally along the second jaw, wherein the second deformable hydraulic member is configured to contain the fluid, and wherein the first and second deformable members are configured to fracture the tissue therebetween in the closed configuration as the first deformable hydraulic member expands from the contracted state to the expanded state.

10. The surgical instrument of claim 9, wherein the second deformable member is configured to expand from the contracted state to the expanded state, and wherein the first and second deformable members are configured to fracture the tissue therebetween in the closed configuration as the first and second deformable hydraulic members expand from the contracted state to the expanded state.

11. The surgical instrument of claim 8, wherein the first jaw includes a longitudinally extending edge, and wherein the first deformable hydraulic member is positioned along at least a portion of the edge.

12. The surgical instrument of claim 7, further comprising a staple cartridge received within the first jaw, the staple cartridge comprising:
   (i) a deck facing the second jaw,
   (ii) a plurality of staple openings formed through the deck, and
   (iii) a plurality of staples positioned respectively within the plurality of staple openings,
   wherein the first deformable hydraulic member extends longitudinally along the deck.

13. The surgical instrument of claim 7, further comprising a pressure control system comprising:
   (i) a fluid actuator configured to direct the fluid into the first deformable member in order to expand the first deformable member from the contracted state to the expanded state,
   (ii) a pressure sensor operatively connected to the first deformable member and configured to sense a measured pressure within the first deformable member, and
   (iii) a controller operatively connected to the fluid actuator and the pressure sensor, wherein the controller is configured to monitor the measured pressure within the first deformable member via the pressure sensor and cease direction of the fluid into the first deformable member via the fluid actuator when the measure pressure increases to a maximum predetermined pressure.

14. The surgical instrument of claim 1, wherein the end effector further includes a pressure relief reservoir fluidly connected to the first deformable member, wherein the first deformable member is configured to contain the fluid up to a maximum predetermined pressure, and wherein an excess pressure greater than the maximum predetermined pressure is configured to direct the fluid from the first deformable member to the pressure relief reservoir such that the deformable member and the pressure relief reservoir are configured to maintain the pressure within the first deformable member to be equal to or less than the maximum predetermined pressure.

15. The surgical instrument of claim 1, wherein the end effector defines a lateral width and a central longitudinal axis bisecting the lateral width, and wherein the at least the portion of the deformable hydraulic member transversely aligns with the central longitudinal axis of the end effector in the expanded state.

16. A staple cartridge, comprising:
(a) a deck extending in a longitudinal direction;
(b) a plurality of staple openings formed through the deck in a transverse direction;
(c) a plurality of staples positioned respectively within the plurality of staple openings and configured to be transversely driven through the plurality of staple openings, respectively; and
(d) a deformable hydraulic member positioned along the deck and configured to contain a fluid therein to expand to an expanded state, wherein at least a portion of the deformable hydraulic member transversely aligns with the deck to extend transversely over the deck in the expanded state, wherein the first deformable hydraulic member with the fluid contained therein is configured to fracture tissue.

17. The surgical instrument of claim 16, wherein the first deformable hydraulic member is configured to expand from a contracted state to the expanded state upon receiving the fluid therein.

18. A method of operating on a tissue with a deformable hydraulic member configured to contain a fluid, the method comprising directing the deformable hydraulic member against a portion of the tissue thereby fracturing the portion of the tissue for severing the tissue.

19. The method of claim 18, further comprising expanding the deformable hydraulic member from a contracted state to an expanded state.

20. The method of claim 19, wherein the tissue is a liver parenchyma tissue, and the method further includes inserting the deformable hydraulic member into the liver parenchyma tissue.

* * * * *